(12) United States Patent
Watanabe et al.

(10) Patent No.: US 6,277,596 B1
(45) Date of Patent: Aug. 21, 2001

(54) **REGULATORY SEQUENCE OF CELLULASE CBH1 GENES ORIGINATING IN *TRICHODERMA VIRIDE* AND SYSTEM FOR MASS-PRODUCING PROTEINS OR PEPTIDES THEREWITH**

(75) Inventors: Manabu Watanabe; Tatsuki Moriya; Kaoru Aoyagi; Naomi Sumida; Takeshi Murakami, all of Odawara (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/254,733
(22) PCT Filed: Sep. 16, 1997
(86) PCT No.: PCT/JP97/03268
  § 371 Date: May 7, 1999
  § 102(e) Date: May 7, 1999
(87) PCT Pub. No.: WO98/11239
  PCT Pub. Date: Mar. 19, 1998

(30) Foreign Application Priority Data

Sep. 13, 1996 (JP) .................................................. 8-243695

(51) Int. Cl.$^7$ .............................. C12P 21/06; C12N 9/00; C12N 1/20; C12N 15/00
(52) U.S. Cl. ................. 435/69.1; 435/252.3; 435/254.6; 435/320.1; 536/24.1
(58) Field of Search .............................. 435/177.12, 200, 435/263, 264, 277, 278, 325, 320.1, 69.1, 254.3, 252.3, 254.6; 536/23.2, 24.3, 24.1

(56) References Cited

FOREIGN PATENT DOCUMENTS

| | | |
|---|---|---|
| 5-509223 | 12/1993 | (JP) . |
| WO 91/17243 | * 11/1991 | (WO) . |
| WO 95/16782 | * 6/1995 | (WO) . |

OTHER PUBLICATIONS

Shoemaker et al. Molecular cloning of . . . T.reesie strain L27. Bio/Technology vol. 1:691–95. 1983.*
Harkki et al. A novel fungal expression system. Bio/Technology vol. 7:596–603. 1989.*
Uusitalo et al. enzyme production by recombinant T.reseei strains. J Biotechnology. vol. 17:35–50. 1991.*
Saarrelainen et al. Cloning, sequencing and enhanced expression. Mol. Gen. Genet. vol. 241: 497–503. 1993.*
Udaka et al. GenBank Accession No. X53931, dated Apr. 10, 1993.*
C. Cheng et al., "Nucleotide sequence of the cellobiohydrolase gene from *Trichoderma viride*", Nucleic Acids Research, vol. 18, No. 18, p. 5559.
W. Sung et al., "Expression of *Trichoderma reesei* and *Trichoderma viride* xylanases in *Escherichia coli*", Biochemistry and Cell Biology, vol. 73, Nos. 5 and 6, pp. 253–259, 1995.
C. Cheng et al., "Efficient Production of Taka–amylase A by *Trichoderma viride*", Agricultural and Biological Chemistry, vol. 55, No. 7, pp. 1817–1822, 1991.
D. Kim et al., "Purification and Characterization of Endoglucanase and Exoglucanase Components from *Trichoderma viride*", Journal of Fermentation and Bioengineering, vol. 77, No. 4, pp. 363–369, 1994.

* cited by examiner

Primary Examiner—Rebecca E. Prouty
Assistant Examiner—Manjunath N. Rao
(74) Attorney, Agent, or Firm—Wenderoth, Lind & Ponack, L.L.P.

(57) ABSTRACT

A high-yield production system for proteins and peptides has been established, and especially a high-yield production system for cellulase in *Trichoderma viride* and similar filamentous fungi. The cellulase cbh1 gene regulator sequence derived from *Trichoderma viride* gives high expression of target proteins. The regulator sequence can therefore be used for high-yield expression of target proteins, especially cellulase. In particular, 15 g/L of an endoglucanase derived from *Humicola insolens* was successfully produced with this regulator sequence.

24 Claims, 7 Drawing Sheets

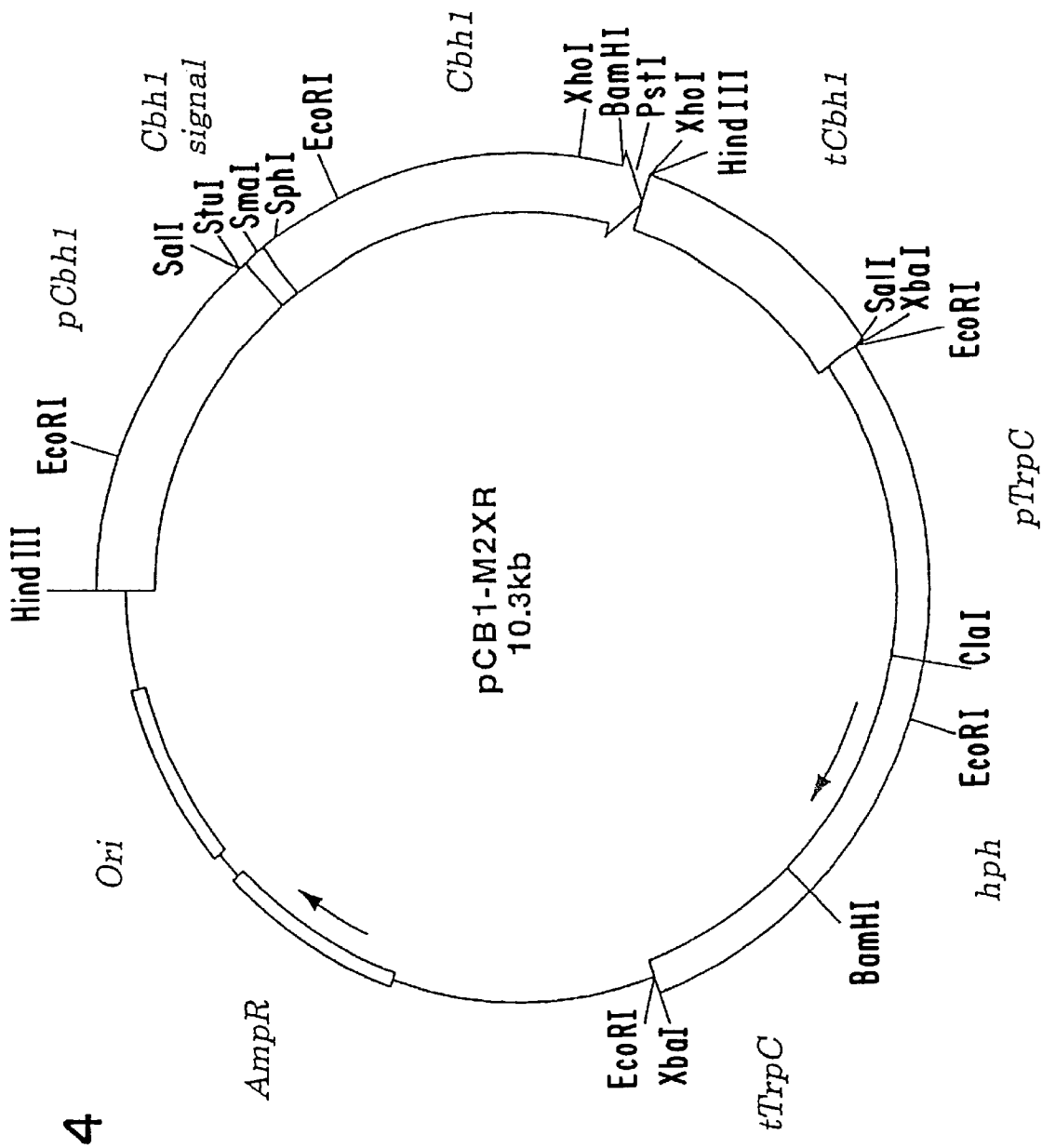
F I G. 4

SEQUENCE LISTING

```
<160> NUMBER OF SEQ ID NOS: 52

<210> SEQ ID NO 1
<211> LENGTH: 4176
<212> TYPE: DNA
<213> ORGANISM: TRICHODERMA VIRIDE MC300-1
<220> FEATURE:
<221> NAME/KEY: sig_peptide
<222> LOCATION: (1438)..(1488)
<220> FEATURE:
<221> NAME/KEY: CDS
<222> LOCATION: (1438)..(1488)
<220> FEATURE:
<221> NAME/KEY: mat_peptide
<222> LOCATION: (1489)..(3108)
<220> FEATURE:
<221> NAME/KEY: CDS
<222> LOCATION: (1489)..(1898)
<220> FEATURE:
<221> NAME/KEY: intron
<222> LOCATION: (1899)..(1965)
<220> FEATURE:
<221> NAME/KEY: CDS
<222> LOCATION: (1966)..(2662)
<220> FEATURE:
<221> NAME/KEY: intron
<222> LOCATION: (2663)..(2724)
<220> FEATURE:
<221> NAME/KEY: CDS
<222> LOCATION: (2725)..(3108)

<400> SEQUENCE: 1
aagcttccat ttggcggctg aataccctga gaatgaaaac acatcaggct gggtgatatc      60
catgaagaca ggtggtgaat atgtaatcac gtccgttctc ctgaagggaa acccttgtc     120 gtggtcacat gcggctcttt ccatgtaagt cggatattcc taagtagcga tggagcggca     180
gaatcaaata ggcaatacag cgagtggctc gaactttta aatgtcgggc gggttgctgc     240
gcttcggcac tagtagacat tgtattccat accccgcccc tgtttccgcg acctctggga     300
```

```
                                                                    -continued ttcccttgaa tgatcaaatt ctcgcctcta ctacctaact cccactgagc ctttacgtct      360
tttgccattc atcctggtgg aagttatcgc ggtgtgtagg gctacatgct aggtcaactg      420
gacgtgttgg ggcccggacc cgaacctaat tttatacaac gactttgatt cagtctacag      480
taatgggacg tccccatata cagttgcacg tagggcacaa cggtagagta cgttgggtga      540
attcgatatg atacgaggat aaccccctga atgtagagtc tcacggcaaa ctctgaccgc      600
gcggtgcgac ctcacaaaac aatacaaacg gatggctaaa agtacatgag ttaatgccta      660
aagatgtcat ataccagcgg ctaataattg tacaattaag tggctaaacg taccgtaatt      720
tgccaatgac ttgtagggtt gcagaagcaa cagtacagcc ccacttcccc acgtttgccc      780
tcttacacgc aggtctaacc tcaactgatg atctcccatc taagttctct tgttgttgtt      840
tagtctaaga ggcaagtgtt tacttcagga ttttgtaagg cgtagcatgt aagaaataaa      900
cagaaagcag acgccaagaa gcgagtttct ggatgaaggc gtttgagaga accttgcagg      960
gagttgtctg acaatagaaa aacaatggat tgtcgcttct actcaggtgt ctgtaattaa     1020
atgttactcc gtcctgtaca ggcaaaaaat atagtcgaat ctgcctaaga tctcgggcct     1080
tcgggccttt aagtctacag gtcagtttgg ttatatgggc attttgggt gtggtagcat      1140 tgagggaacc actgcttttg ccaaggagct gaacgtatgc tgtaggcaaa gctctaggtg     1200
ccactgcatt tgtgtcgaac ataatgtgat gcttgggcag gcataatagc cgccaaagat     1260
agcctcattg agcggaagtc ggcgaacagg tgaagagcag aatatcacat atatatatgg     1320
cccaaacgcc gtgtcccctt ctcccttttcc ccatctactc atcaactcag atcctccaga    1380
agacttgtac atcatctttt ggggcatagc attctagtcg actacggact gcgcatc        1437 atg tat caa aag ttg gcc ctc atc tcg gcc ttc ttg gct act gct cgt       1485
Met Tyr Gln Lys Leu Ala Leu Ile Ser Ala Phe Leu Ala Thr Ala Arg
        -15                 -10                 -5 gct cag tcg gcc tgc acc ctc cag gcg gaa act cac ccg cct ctg aca       1533
Ala Gln Ser Ala Cys Thr Leu Gln Ala Glu Thr His Pro Pro Leu Thr
 -1   1               5                  10                  15 tgg cag aaa tgc tca tct ggt ggc act tgc acc caa cag aca ggc tcc       1581
Trp Gln Lys Cys Ser Ser Gly Gly Thr Cys Thr Gln Gln Thr Gly Ser
                20                  25                  30 gtg gtc atc gac gcg aac tgg cgc tgg act cac gcc acc aac agc agc       1629
Val Val Ile Asp Ala Asn Trp Arg Trp Thr His Ala Thr Asn Ser Ser
            35                  40                  45 acg aac tgc tac gac ggc aat act tgg agc tca acc ctg tgc cct gac       1677
Thr Asn Cys Tyr Asp Gly Asn Thr Trp Ser Ser Thr Leu Cys Pro Asp
        50                  55                  60 aat gag act tgc gcg aag aac tgc tgc ttg gac ggt gct gcc tac gcg       1725
Asn Glu Thr Cys Ala Lys Asn Cys Cys Leu Asp Gly Ala Ala Tyr Ala
    65                  70                  75 tcc acg tac gga gtc acc acg agc gct gac agc ctc tcc att ggc ttc       1773
Ser Thr Tyr Gly Val Thr Thr Ser Ala Asp Ser Leu Ser Ile Gly Phe
 80                  85                  90                  95 gtc act cag tct gcg caa aag aac gtc ggc gct cgt ctc tac ttg atg       1821
Val Thr Gln Ser Ala Gln Lys Asn Val Gly Ala Arg Leu Tyr Leu Met
                100                 105                 110 gcg agt gac acg acc tat caa gaa ttc acc ctg ctt ggc aac gag ttc       1869
Ala Ser Asp Thr Thr Tyr Gln Glu Phe Thr Leu Leu Gly Asn Glu Phe
            115                 120                 125 tct ttc gat gtt gat gtt tcg cag ctg cc gtaagtgacc aactacacct          1918
Ser Phe Asp Val Asp Val Ser Gln Leu Pro
        130                 135 cttgatgcca ttctcgtatt agttctcagc tgactagctt atttaag a tgt ggc ttg     1975
```

```
                                                Cys Gly Leu
                                                       140 aac gga gct ctt tac ttc gtg tcc atg gac gcg gat ggt ggc gtg agc     2023
Asn Gly Ala Leu Tyr Phe Val Ser Met Asp Ala Asp Gly Gly Val Ser
            145                 150                 155 aag tat ccc acc aac act gcc ggt gcc aag tac ggc acg ggc tac tgt     2071
Lys Tyr Pro Thr Asn Thr Ala Gly Ala Lys Tyr Gly Thr Gly Tyr Cys
                160                 165                 170 gac agc cag tgc cct cgt gat ctc aag ttc atc aac ggc cag gcc aat     2119
Asp Ser Gln Cys Pro Arg Asp Leu Lys Phe Ile Asn Gly Gln Ala Asn
            175                 180                 185 gtt gag ggc tgg gag ccg tcc tct aac aat gcc aac acg ggc att ggc     2167
Val Glu Gly Trp Glu Pro Ser Ser Asn Asn Ala Asn Thr Gly Ile Gly
        190                 195                 200 gga cat gga agc tgc tgc tct gag atg gat atc tgg gag gcc aat tcc     2215
Gly His Gly Ser Cys Cys Ser Glu Met Asp Ile Trp Glu Ala Asn Ser
205                 210                 215                 220 atc tct gag gct ctt act cct cat cct tgc acg acc gtc ggg cag gaa     2263
Ile Ser Glu Ala Leu Thr Pro His Pro Cys Thr Thr Val Gly Gln Glu
                225                 230                 235 att tgc gac ggt gac tcc tgc ggt gga acc tac tcg ggt gac cga tat     2311
Ile Cys Asp Gly Asp Ser Cys Gly Gly Thr Tyr Ser Gly Asp Arg Tyr
            240                 245                 250 ggc ggt act tgc gac cct gat ggc tgc gat tgg aac cca tat cgc ttg     2359
Gly Gly Thr Cys Asp Pro Asp Gly Cys Asp Trp Asn Pro Tyr Arg Leu
                255                 260                 265 ggc aac acc agc ttc tat ggc ccc ggc tcc agc ttc acg ctt gac acc     2407
Gly Asn Thr Ser Phe Tyr Gly Pro Gly Ser Ser Phe Thr Leu Asp Thr
        270                 275                 280 acc aag aag ttg acc gtc gtc act cag ttc gag act tcg ggt gcc atc     2455
Thr Lys Lys Leu Thr Val Val Thr Gln Phe Glu Thr Ser Gly Ala Ile
285                 290                 295                 300 aac cga tac tat gtc cag aat ggc gtc act ttc cag cag ccc aac gcc     2503
Asn Arg Tyr Tyr Val Gln Asn Gly Val Thr Phe Gln Gln Pro Asn Ala
                305                 310                 315 gag ctc ggt gat tac tct ggc aac tcg ctc gac gat gac tac tgc gcg     2551
Glu Leu Gly Asp Tyr Ser Gly Asn Ser Leu Asp Asp Asp Tyr Cys Ala
            320                 325                 330 gct gaa gag gcg gag ttt ggc ggc tcc tct ttc tcg gac aag ggc ggc     2599
Ala Glu Glu Ala Glu Phe Gly Gly Ser Ser Phe Ser Asp Lys Gly Gly
                335                 340                 345 ctt act caa ttc aag aag gct act tcc ggt ggc atg gtc ctg gtc atg     2647
Leu Thr Gln Phe Lys Lys Ala Thr Ser Gly Gly Met Val Leu Val Met
        350                 355                 360 agc ctg tgg gat gac gtgagttcaa gaataacatt cacattgtca acagaatgac    2702
Ser Leu Trp Asp Asp
365 agaactgact gagagacgat ag tac tac gcc aac atg ctg tgg ctg gac tct   2754
                        Tyr Tyr Ala Asn Met Leu Trp Leu Asp Ser
                                370                 375 acc tac ccg acg aac gag acc tcc tcc acc ccc ggt gcc gtg cgt gga    2802
Thr Tyr Pro Thr Asn Glu Thr Ser Ser Thr Pro Gly Ala Val Arg Gly
380                 385                 390                 395 agc tgc tcc acc agc tcc ggt gtt cct gct cag ctc gag tcc aac tct    2850
Ser Cys Ser Thr Ser Ser Gly Val Pro Ala Gln Leu Glu Ser Asn Ser
                400                 405                 410 ccc aac gcc aag gtc gta tac tcc aac atc aag ttc ggc ccc atc ggc    2898
Pro Asn Ala Lys Val Val Tyr Ser Asn Ile Lys Phe Gly Pro Ile Gly
            415                 420                 425
```

```
agc acc ggc aac tct agc ggc gga aac cct cct ggc gga aac cct ccc    2946
Ser Thr Gly Asn Ser Ser Gly Gly Asn Pro Pro Gly Gly Asn Pro Pro
        430                 435                 440 ggc acc aca acc acc cgc cgc ccg gct acc tcc act gga agc tct ccc    2994
Gly Thr Thr Thr Thr Arg Arg Pro Ala Thr Ser Thr Gly Ser Ser Pro
    445                 450                 455 ggc cct act cag acg cac tat ggc cag tgc ggt gga att gga tac tcg    3042
Gly Pro Thr Gln Thr His Tyr Gly Gln Cys Gly Gly Ile Gly Tyr Ser
460                 465                 470                 475 ggc ccc acc gtc tgc gcg agt ggc agc act tgc cag gtc ctg aac ccc    3090
Gly Pro Thr Val Cys Ala Ser Gly Ser Thr Cys Gln Val Leu Asn Pro
                480                 485                 490 tac tac tct cag tgc ttg taa ggtactgtg gcaaagctt gaggtactgc         3140
Tyr Tyr Ser Gln Cys Leu
            495 tggcttatgg atgagttcat ctcattatgg actagatgga ggatttactt tgctgtatct   3200
acttctgagg cttccaatat atacggttat ttcacctttg ctggaatgct cgctagcttg   3260
gcaagcacgg ctttcgagag acggactgat tctctgctaa ctatgcatta tataagactg   3320
aaatagacaa aaaaggaaaa aagttgccac tcgaattatc ttgacggtgt tgattatatg   3380
tatggcattg taaggggtttt tcattgatat ttctcccgcc aatatggttc tactcccatc   3440
tccgcgaatc tccttttctc gaaggccgta gtggcacgcc aattggcaac aacccacagg   3500
gagacgaaaa acatgatggc ggcagccgaa atcagtggcg caatgattga aaacacggtg   3560
agaccgtagc ttgcagcctg gaaagcactg ttggagacca gcttgtccgt tgcgaggccg   3620
acttgcattg ctgtcaagac gatggcaatg tagccgagca ctgtcaccag ggacgcaaag   3680
ttgtcgcgga taaggtctcc gtagatggcg tagccagaga ttcgagaata gcctctcaaa   3740
aggtggccct ttcgaaaccg gtaaatcttg ttcaagcgtc ctaggcgcag ctcgccgtac   3800
cagtagcggg gattgacagc agaatagcag tgattctcca ggacttgact ggacaatatc   3860
ttccagtact cccaagatac aatatccggc aagagtccct tctcacgtgc gaggcgaaag   3920
tcgctgtagt gcgcaatgag agcgcagtag gagaatagaa acccctggc acattgttct   3980
acctcggcgt gtagtggatg actgtcgggc agaatgtgct gtctccagaa tccgatgtct   4040
agtagatact ctggcagagg cttcaggtga atgcccttgg gacccagat gagatgcagc    4100
tccggattct cagtaacgac gatctcgcgg gagagcacga gttggtgatg aagagggcga   4160
ggaggcatgg gtcgac                                                   4176
```

<210> SEQ ID NO 2
<211> LENGTH: 514
<212> TYPE: PRT
<213> ORGANISM: TRICHODERMA VIRIDE MC300-1

<400> SEQUENCE: 2

```
Met Tyr Gln Lys Leu Ala Leu Ile Ser Ala Phe Leu Ala Thr Ala Arg
            -15                 -10                 -5

Ala Gln Ser Ala Cys Thr Leu Gln Ala Glu Thr His Pro Pro Leu Thr
 -1  1               5                  10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
                35                  40                  45

Thr Asn Cys Tyr Asp Gly Asn Thr Trp Ser Ser Thr Leu Cys Pro Asp
            50                  55                  60
```

-continued

```
Asn Glu Thr Cys Ala Lys Asn Cys Cys Leu Asp Gly Ala Ala Tyr Ala
     65                  70                  75
Ser Thr Tyr Gly Val Thr Thr Ala Asp Ser Leu Ser Ile Gly Phe
 80                  85                  90                  95
Val Thr Gln Ser Ala Gln Lys Asn Val Gly Ala Arg Leu Tyr Leu Met
                100                 105                 110
Ala Ser Asp Thr Thr Tyr Gln Glu Phe Thr Leu Leu Gly Asn Glu Phe
            115                 120                 125
Ser Phe Asp Val Asp Val Ser Gln Leu Pro Cys Gly Leu Asn Gly Ala
        130                 135                 140
Leu Tyr Phe Val Ser Met Asp Ala Asp Gly Gly Val Ser Lys Tyr Pro
    145                 150                 155
Thr Asn Thr Ala Gly Ala Lys Tyr Gly Thr Gly Tyr Cys Asp Ser Gln
160                 165                 170                 175
Cys Pro Arg Asp Leu Lys Phe Ile Asn Gly Gln Ala Asn Val Glu Gly
                180                 185                 190
Trp Glu Pro Ser Ser Asn Asn Ala Asn Thr Gly Ile Gly Gly His Gly
            195                 200                 205
Ser Cys Cys Ser Glu Met Asp Ile Trp Glu Ala Asn Ser Ile Ser Glu
        210                 215                 220
Ala Leu Thr Pro His Pro Cys Thr Thr Val Gly Gln Glu Ile Cys Asp
    225                 230                 235
Gly Asp Ser Cys Gly Gly Thr Tyr Ser Gly Asp Arg Tyr Gly Gly Thr
240                 245                 250                 255
Cys Asp Pro Asp Gly Cys Asp Trp Asn Pro Tyr Arg Leu Gly Asn Thr
                260                 265                 270
Ser Phe Tyr Gly Pro Gly Ser Ser Phe Thr Leu Asp Thr Thr Lys Lys
            275                 280                 285
Leu Thr Val Val Thr Gln Phe Glu Thr Ser Gly Ala Ile Asn Arg Tyr
        290                 295                 300
Tyr Val Gln Asn Gly Val Thr Phe Gln Gln Pro Asn Ala Glu Leu Gly
    305                 310                 315
Asp Tyr Ser Gly Asn Ser Leu Asp Asp Tyr Cys Ala Ala Glu Glu
320                 325                 330                 335
Ala Glu Phe Gly Gly Ser Ser Phe Ser Asp Lys Gly Gly Leu Thr Gln
                340                 345                 350
Phe Lys Lys Ala Thr Ser Gly Gly Met Val Leu Val Met Ser Leu Trp
            355                 360                 365
Asp Asp Tyr Tyr Ala Asn Met Leu Trp Leu Asp Ser Thr Tyr Pro Thr
        370                 375                 380
Asn Glu Thr Ser Ser Thr Pro Gly Ala Val Arg Gly Ser Cys Ser Thr
    385                 390                 395
Ser Ser Gly Val Pro Ala Gln Leu Glu Ser Asn Ser Pro Asn Ala Lys
400                 405                 410                 415
Val Val Tyr Ser Asn Ile Lys Phe Gly Pro Ile Gly Ser Thr Gly Asn
                420                 425                 430
Ser Ser Gly Gly Asn Pro Pro Gly Gly Asn Pro Gly Thr Thr Thr
            435                 440                 445
Thr Arg Arg Pro Ala Thr Ser Thr Gly Ser Ser Pro Gly Pro Thr Gln
        450                 455                 460
Thr His Tyr Gly Gln Cys Gly Gly Ile Gly Tyr Ser Gly Pro Thr Val
    465                 470                 475
Cys Ala Ser Gly Ser Thr Cys Gln Val Leu Asn Pro Tyr Tyr Ser Gln
```

```
480             485             490             495

Cys Leu

<210> SEQ ID NO 3
<211> LENGTH: 286
<212> TYPE: PRT
<213> ORGANISM: Humicola insolens

<400> SEQUENCE: 3

Ala Cys Ala Asp Gly Lys Ser Thr Arg Tyr Trp Asp Cys Cys Lys Pro
 -2   1           5                  10

Ser Cys Gly Trp Ala Lys Lys Ala Pro Val Asn Gln Pro Val Phe Ser
 15              20                  25                      30

Cys Asn Ala Asn Phe Gln Arg Leu Thr Asp Phe Asp Ala Lys Ser Gly
                 35                  40                  45

Cys Glu Pro Gly Gly Val Ala Tyr Ser Cys Ala Asp Gln Thr Pro Trp
             50                  55                  60

Ala Val Asn Asp Asp Phe Ala Phe Gly Phe Ala Ala Thr Ser Ile Ala
             65                  70                  75

Gly Ser Asn Glu Ala Gly Trp Cys Cys Ala Cys Tyr Glu Leu Thr Phe
         80                  85                  90

Thr Ser Gly Pro Val Ala Gly Lys Lys Met Val Val Gln Ser Thr Ser
 95             100                 105                     110

Thr Gly Gly Asp Leu Gly Ser Asn His Phe Asp Leu Asn Ile Pro Gly
                115                 120                 125

Gly Gly Val Gly Ile Phe Asp Gly Cys Thr Pro Gln Phe Gly Gly Leu
            130                 135                 140

Pro Gly Gln Arg Tyr Gly Gly Ile Ser Ser Arg Asn Glu Cys Asp Arg
            145                 150                 155

Phe Pro Asp Ala Leu Lys Pro Gly Cys Tyr Trp Arg Phe Asp Trp Phe
            160                 165                 170

Lys Asn Ala Asp Asn Pro Ser Phe Ser Phe Arg Gln Val Gln Cys Pro
175                 180                 185                 190

Ala Glu Leu Val Ala Arg Thr Gly Cys Arg Arg Asn Asp Asp Gly Asn
                195                 200                 205

Phe Pro Ala Val Gln Ile Pro Ser Ser Ser Thr Ser Ser Pro Val Gly
            210                 215                 220

Gln Pro Thr Ser Thr Ser Thr Ser Thr Ser Thr Thr Ser Ser Pro
            225                 230                 235

Pro Val Gln Pro Thr Thr Pro Ser Gly Cys Thr Ala Glu Arg Trp Ala
240                 245                 250

Gln Cys Gly Gly Asn Gly Trp Ser Gly Cys Thr Thr Cys Val Ala Gly
255                 260                 265                 270

Ser Thr Cys Thr Lys Ile Asn Asp Trp Tyr His Gln Cys Leu
                275                 280

<210> SEQ ID NO 4
<211> LENGTH: 927
<212> TYPE: DNA
<213> ORGANISM: Humicola insolens
<220> FEATURE:
<221> NAME/KEY: CDS
<222> LOCATION: (1)..(6)
<220> FEATURE:
<221> NAME/KEY: CDS
<222> LOCATION: (7)..(278)
<220> FEATURE:
<221> NAME/KEY: intron
```

-continued

```
<222> LOCATION: (279)..(334)
<220> FEATURE:
<221> NAME/KEY: CDS
<222> LOCATION: (335)..(914)
<220> FEATURE:
<221> NAME/KEY: mat_peptide
<222> LOCATION: (7)..(914)

<400> SEQUENCE: 4
```

| | | | | | | | | | | | | | | | | |
|---|---|---|---|---|---|---|---|---|---|---|---|---|---|---|---|---|
| gca | tgc | gct | gat | ggc | aag | tcc | acc | cgc | tac | tgg | gac | tgc | tgc | aag | cct | 48 |
| Ala | Cys | Ala | Asp | Gly | Lys | Ser | Thr | Arg | Tyr | Trp | Asp | Cys | Cys | Lys | Pro | |
| -2 | | 1 | | | 5 | | | | | 10 | | | | | | |
| tcg | tgc | ggc | tgg | gcc | aag | aag | gct | ccc | gtg | aac | cag | cct | gtc | ttc | tcc | 96 |
| Ser | Cys | Gly | Trp | Ala | Lys | Lys | Ala | Pro | Val | Asn | Gln | Pro | Val | Phe | Ser | |
| 15 | | | | | 20 | | | | | 25 | | | | | 30 | |
| tgc | aac | gcc | aac | ttc | cag | cgt | ctc | act | gac | ttc | gac | gcc | aag | tcc | ggc | 144 |
| Cys | Asn | Ala | Asn | Phe | Gln | Arg | Leu | Thr | Asp | Phe | Asp | Ala | Lys | Ser | Gly | |
| | | | | 35 | | | | | 40 | | | | | 45 | | |
| tgc | gag | ccg | ggc | ggt | gtc | gcc | tac | tcg | tgc | gcc | gac | cag | acc | cca | tgg | 192 |
| Cys | Glu | Pro | Gly | Gly | Val | Ala | Tyr | Ser | Cys | Ala | Asp | Gln | Thr | Pro | Trp | |
| | | 50 | | | | | 55 | | | | | 60 | | | | |
| gct | gtg | aac | gac | gac | ttc | gcg | ttc | ggt | ttt | gct | gcc | acc | tct | att | gcc | 240 |
| Ala | Val | Asn | Asp | Asp | Phe | Ala | Phe | Gly | Phe | Ala | Ala | Thr | Ser | Ile | Ala | |
| | 65 | | | | | 70 | | | | | 75 | | | | | |
| ggc | agc | aat | gag | gcg | ggc | tgg | tgc | tgc | gcc | tgc | tac | ga | gtaagctttg | | | 288 |
| Gly | Ser | Asn | Glu | Ala | Gly | Trp | Cys | Cys | Ala | Cys | Tyr | Glu | | | | |
| 80 | | | | | 85 | | | | | 90 | | | | | | |

| | | | | |
|---|---|---|---|---|
| gtcgcgtgtg | taacactgtg | caggcatagc | actaaccacc | tcccag g ctc acc | 341 |
| | | | | Leu Thr | |

| | | | | | | | | | | | | | | | | |
|---|---|---|---|---|---|---|---|---|---|---|---|---|---|---|---|---|
| tcc | aca | tcc | ggt | cct | gtt | gct | ggc | aag | aag | atg | gtc | gtc | cag | tcc | acc | 389 |
| Phe | Thr | Ser | Gly | Pro | Val | Ala | Gly | Lys | Lys | Met | Val | Val | Gln | Ser | Thr | |
| | 95 | | | | 100 | | | | | 105 | | | | | | |
| agc | act | ggc | ggt | gat | ctt | ggc | agc | aac | cac | ttc | gat | ctc | aac | atc | ccc | 437 |
| Ser | Thr | Gly | Gly | Asp | Leu | Gly | Ser | Asn | His | Phe | Asp | Leu | Asn | Ile | Pro | |
| 110 | | | | | 115 | | | | | 120 | | | | | 125 | |
| ggc | ggc | ggc | gtc | ggc | atc | ttc | gac | gga | tgc | act | ccc | cag | ttc | ggc | ggt | 485 |
| Gly | Gly | Gly | Val | Gly | Ile | Phe | Asp | Gly | Cys | Thr | Pro | Gln | Phe | Gly | Gly | |
| | | | | 130 | | | | | 135 | | | | | 140 | | |
| ctg | ccc | ggc | cag | cgc | tac | ggc | ggc | atc | tcg | tcc | cgc | aac | gag | tgc | gat | 533 |
| Leu | Pro | Gly | Gln | Arg | Tyr | Gly | Gly | Ile | Ser | Ser | Arg | Asn | Glu | Cys | Asp | |
| | | | | 145 | | | | | 150 | | | | | 155 | | |
| cgg | ttc | ccc | gac | gcc | ctc | aag | ccc | ggc | tgc | tac | tgg | cgc | ttc | gac | tgg | 581 |
| Arg | Phe | Pro | Asp | Ala | Leu | Lys | Pro | Gly | Cys | Tyr | Trp | Arg | Phe | Asp | Trp | |
| | | | | 160 | | | | | 165 | | | | | 170 | | |
| ttc | aag | aac | gcc | gac | aac | ccg | agc | ttc | agc | ttc | cgt | cag | gtc | caa | tgc | 629 |
| Phe | Lys | Asn | Ala | Asp | Asn | Pro | Ser | Phe | Ser | Phe | Arg | Gln | Val | Gln | Cys | |
| | 175 | | | | | 180 | | | | | 185 | | | | | |
| cca | gcc | gag | ctc | gtc | gct | cgc | acc | gga | tgc | cgc | cgc | aac | gac | gac | ggc | 677 |
| Pro | Ala | Glu | Leu | Val | Ala | Arg | Thr | Gly | Cys | Arg | Arg | Asn | Asp | Asp | Gly | |
| 190 | | | | | 195 | | | | | 200 | | | | | 205 | |
| aac | ttc | cct | gcc | gtc | cag | atc | ccc | tcc | agc | agc | acc | agc | tct | ccg | gtc | 725 |
| Asn | Phe | Pro | Ala | Val | Gln | Ile | Pro | Ser | Ser | Ser | Thr | Ser | Ser | Pro | Val | |
| | | | | 210 | | | | | 215 | | | | | 220 | | |
| ggc | cag | cct | acc | agt | acc | agc | acc | acc | tcc | acc | tcc | acc | acc | tcg | agc | 773 |
| Gly | Gln | Pro | Thr | Ser | Thr | Ser | Thr | Thr | Ser | Thr | Ser | Thr | Thr | Ser | Ser | |
| | | | 225 | | | | | 230 | | | | | 235 | | | |
| ccg | ccc | gtc | cag | cct | acg | act | ccc | agc | ggc | tgc | act | gct | gag | agg | tgg | 821 |
| Pro | Pro | Val | Gln | Pro | Thr | Thr | Pro | Ser | Gly | Cys | Thr | Ala | Glu | Arg | Trp | |
| | | 240 | | | | | 245 | | | | | 250 | | | | |
| gct | cag | tgc | ggc | ggc | aat | ggc | tgg | agc | ggc | tgc | acc | acc | tgc | gtc | gct | 869 |

-continued

```
Ala Gln Cys Gly Gly Asn Gly Trp Ser Gly Cys Thr Thr Cys Val Ala
255                 260                 265                 270 ggc agc acc tgc acg aag att aat gac tgg tac cat cag tgc ctg taa       917
Gly Ser Thr Cys Thr Lys Ile Asn Asp Trp Tyr His Gln Cys Leu
                275                 280                 285 ggtagtc gac                                                            927
```

<210> SEQ ID NO 5
<211> LENGTH: 418
<212> TYPE: PRT
<213> ORGANISM: TRICHODERMA VIRIDE MC300-1

<400> SEQUENCE: 5

```
Met Asn Arg Thr Met Ala Pro Leu Leu Ala Ser Ile Leu Phe
        -20                 -15                 -10

Gly Gly Ala Ala Ala Gln Gln Thr Val Trp Gly Gln Cys Gly Gly Ile
 -5                   1                   5                  10

Gly Trp Ser Gly Pro Thr Ser Cys Ala Pro Gly Ser Ala Cys Ser Thr
                 15                  20                  25

Leu Asn Pro Tyr Tyr Ala Gln Cys Ile Pro Gly Ala Thr Ser Ile Thr
             30                  35                  40

Thr Ser Thr Arg Pro Pro Ser Gly Pro Thr Thr Thr Arg Ala Thr
         45                  50                  55

Ser Thr Ser Ser Pro Pro Thr Ser Ser Gly Val Arg Phe Ala
 60                  65                  70                  75

Gly Val Asn Ile Ala Gly Phe Asp Phe Gly Cys Thr Thr Asp Gly Thr
                 80                  85                  90

Cys Val Thr Ser Lys Val Tyr Pro Pro Leu Lys Asn Phe Thr Gly Ala
                 95                 100                 105

Asn Asn Tyr Pro Asp Gly Ile Gly Gln Met Gln His Phe Val Asn Asp
            110                 115                 120

Asp Gly Met Thr Ile Phe Arg Leu Pro Val Gly Trp Gln Tyr Leu Val
        125                 130                 135

Asn Asn Asn Leu Gly Gly Thr Leu Asp Ser Thr Ser Ile Ser Lys Tyr
140                 145                 150                 155

Asp Gln Leu Val Gln Gly Cys Leu Ser Leu Gly Val Tyr Cys Ile Ile
            160                 165                 170

Asp Ile His Asn Tyr Ala Arg Trp Asn Gly Gly Ile Ile Gly Gln Gly
        175                 180                 185

Gly Pro Thr Asn Ala Gln Phe Thr Ser Leu Trp Ser Gln Leu Ala Ser
        190                 195                 200

Lys Tyr Ala Ser Gln Ser Arg Val Trp Phe Gly Ile Met Asn Glu Pro
205                 210                 215

His Asp Val Asn Ile Asn Thr Trp Ala Ala Thr Val Gln Glu Val Val
220                 225                 230                 235

Thr Ala Ile Arg Asn Ala Gly Ala Thr Ser Gln Tyr Ile Ser Leu Pro
            240                 245                 250

Gly Asn Asp Tyr Gln Ser Ala Ala Phe Ile Ser Asp Gly Ser Ala
            255                 260                 265

Ala Ala Leu Ser Gln Val Thr Asn Pro Asp Gly Ser Thr Thr Asn Leu
        270                 275                 280

Ile Phe Asp Val His Lys Tyr Leu Asp Ser Asp Asn Ser Gly Thr His
        285                 290                 295

Ala Glu Cys Thr Thr Asn Asn Ile Asp Gly Ala Phe Ala Pro Leu Ala
300                 305                 310                 315
```

-continued

```
Thr Trp Leu Arg Gln Asn Asn Arg Gln Ala Ile Leu Thr Glu Thr Gly
            320                 325                 330

Gly Gly Asn Val Gln Ser Cys Ile Gln Asp Leu Cys Gln Gln Ile Gln
            335                 340                 345

Tyr Leu Asn Gln Asn Ser Asp Val Tyr Leu Gly Tyr Ala Gly Trp Gly
            350                 355                 360

Ala Gly Ser Phe Asp Ser Thr Tyr Ile Leu Thr Glu Thr Pro Thr Gly
        365                 370                 375

Ser Gly Asn Ser Trp Thr Asp Thr Ser Leu Val Ser Ser Cys Leu Ala
380                 385                 390                 395

Arg Lys

<210> SEQ ID NO 6
<211> LENGTH: 1463
<212> TYPE: DNA
<213> ORGANISM: TRICHODERMA VIRIDE MC300-1
<220> FEATURE:
<221> NAME/KEY: sig_peptide
<222> LOCATION: (14)..(76)
<220> FEATURE:
<221> NAME/KEY: CDS
<222> LOCATION: (14)..(76)
<220> FEATURE:
<221> NAME/KEY: mat_peptide
<222> LOCATION: (77)..(1450)
<220> FEATURE:
<221> NAME/KEY: CDS
<222> LOCATION: (77)..(342)
<220> FEATURE:
<221> NAME/KEY: intron
<222> LOCATION: (343)..(525)
<220> FEATURE:
<221> NAME/KEY: CDS
<222> LOCATION: (526)..(1450)

<400> SEQUENCE: 6
aggcctgcgc atc atg aac agg acc atg gct cca ttg ctg ctt gca gcg       49
            Met Asn Arg Thr Met Ala Pro Leu Leu Leu Ala Ala
                -20             -15                 -10 tcg ata ctc ttc ggg ggc gct gct gca caa cag act gtc tgg gga cag       97
Ser Ile Leu Phe Gly Gly Ala Ala Ala Gln Gln Thr Val Trp Gly Gln
            -5              -1  1                   5 tgt gga ggt att ggt tgg agc gga cct acg agt tgt gct cct gga tca      145
Cys Gly Gly Ile Gly Trp Ser Gly Pro Thr Ser Cys Ala Pro Gly Ser
        10                  15                  20 gct tgt tct act ctc aat cct tat tat gcg caa tgc att ccg ggg gcc      193
Ala Cys Ser Thr Leu Asn Pro Tyr Tyr Ala Gln Cys Ile Pro Gly Ala
    25                  30                  35 act agt atc acc acc tcg acc cga ccc ccc tcg ggt cca acc acc acc      241
Thr Ser Ile Thr Thr Ser Thr Arg Pro Pro Ser Gly Pro Thr Thr Thr
40                  45                  50                  55 acc aga gcc acc tca acg acc tca tct ccg cca ccg acc agc tct gga      289
Thr Arg Ala Thr Ser Thr Thr Ser Ser Pro Pro Pro Thr Ser Ser Gly
                60                  65                  70 gtt cga ttt gct ggc gtt aac atc gcg ggc ttt gac ttc gga tgt acc      337
Val Arg Phe Ala Gly Val Asn Ile Ala Gly Phe Asp Phe Gly Cys Thr
            75                  80                  85 aca ga gtatgtcttc atgttgcata gtgttgctgg ctgagtattc tgggcggatg        392
Thr Asp atttatagct gtgcgggctg caaaacaccg ccggtctgcc actatcaagg catagttgat    452
aggcggcggt gttttcttca atcccctgat tacactctca agaatctagt ggctgatgga    512
```

```
tgtatgatta cag t ggc act tgc gtt aca tcg aag gtt tat cct ccg ttg        562
              Gly Thr Cys Val Thr Ser Lys Val Tyr Pro Pro Leu
                90                  95                 100 aag aac ttc act ggg gca aac aac tac ccg gac ggt atc ggc cag atg         610
Lys Asn Phe Thr Gly Ala Asn Asn Tyr Pro Asp Gly Ile Gly Gln Met
            105                 110                 115 cag cac ttc gtc aac gat gat ggg atg act att ttc cgc cta ccc gtc         658
Gln His Phe Val Asn Asp Asp Gly Met Thr Ile Phe Arg Leu Pro Val
        120                 125                 130 gga tgg cag tac ctc gta aac aac aat ctg ggt gga act ctc gat tcc         706
Gly Trp Gln Tyr Leu Val Asn Asn Asn Leu Gly Gly Thr Leu Asp Ser
    135                 140                 145 acc agt atc tcg aag tat gat cag ctc gtt cag ggg tgc ctg tct ctc         754
Thr Ser Ile Ser Lys Tyr Asp Gln Leu Val Gln Gly Cys Leu Ser Leu
150                 155                 160                 165 ggt gta tac tgc atc atc gac atc cac aat tat gct cga tgg aac ggt         802
Gly Val Tyr Cys Ile Ile Asp Ile His Asn Tyr Ala Arg Trp Asn Gly
                170                 175                 180 gga atc att ggc cag gga ggc cct aca aat gcc cag ttt acc agt ctt         850
Gly Ile Ile Gly Gln Gly Gly Pro Thr Asn Ala Gln Phe Thr Ser Leu
            185                 190                 195 tgg tcg cag ttg gca tcg aag tac gcg tct cag tcg agg gtg tgg ttc         898
Trp Ser Gln Leu Ala Ser Lys Tyr Ala Ser Gln Ser Arg Val Trp Phe
        200                 205                 210 gga ata atg aat gag ccc cac gac gtg aac atc aac act tgg gct gcc         946
Gly Ile Met Asn Glu Pro His Asp Val Asn Ile Asn Thr Trp Ala Ala
    215                 220                 225 acg gtt caa gag gtc gtc act gca atc cgc aac gcc ggt gct acg tcg         994
Thr Val Gln Glu Val Val Thr Ala Ile Arg Asn Ala Gly Ala Thr Ser
230                 235                 240                 245 caa tac att tct ctg cct gga aat gat tat caa tct gcg gca gct ttt        1042
Gln Tyr Ile Ser Leu Pro Gly Asn Asp Tyr Gln Ser Ala Ala Ala Phe
                250                 255                 260 att tcc gat ggc agt gca gcc gcc ctg tct cag gta acg aac cct gat        1090
Ile Ser Asp Gly Ser Ala Ala Ala Leu Ser Gln Val Thr Asn Pro Asp
            265                 270                 275 gga tca aca acg aat cta atc ttc gat gtc cac aag tac tta gac tcg        1138
Gly Ser Thr Thr Asn Leu Ile Phe Asp Val His Lys Tyr Leu Asp Ser
        280                 285                 290 gac aac tcc ggt act cac gcc gaa tgc act aca aac aac atc gac ggc        1186
Asp Asn Ser Gly Thr His Ala Glu Cys Thr Thr Asn Asn Ile Asp Gly
    295                 300                 305 gcc ttt gct cct ctc gcc act tgg ctt cga cag aac aac cgc cag gct        1234
Ala Phe Ala Pro Leu Ala Thr Trp Leu Arg Gln Asn Asn Arg Gln Ala
310                 315                 320                 325 att ctg acg gaa acc ggc ggt ggc aat gtt cag tcc tgc atc caa gat        1282
Ile Leu Thr Glu Thr Gly Gly Gly Asn Val Gln Ser Cys Ile Gln Asp
                330                 335                 340 ttg tgc caa cag atc cag tac ctc aac cag aac tca gat gtc tat ctt        1330
Leu Cys Gln Gln Ile Gln Tyr Leu Asn Gln Asn Ser Asp Val Tyr Leu
            345                 350                 355 ggc tat gct ggc tgg ggt gcc ggt tca ttt gat agc act tat att ctg        1378
Gly Tyr Ala Gly Trp Gly Ala Gly Ser Phe Asp Ser Thr Tyr Ile Leu
        360                 365                 370 acg gaa acg cct act gga agc ggt aac tcg tgg acg gac aca tcc cta        1426
Thr Glu Thr Pro Thr Gly Ser Gly Asn Ser Trp Thr Asp Thr Ser Leu
    375                 380                 385 gtt agc tcg tgt ctc gcc agg aag taaggtactc gag                          1463
Val Ser Ser Cys Leu Ala Arg Lys
90                  395
```

<210> SEQ ID NO 7
<211> LENGTH: 223
<212> TYPE: PRT
<213> ORGANISM: TRICHODERMA VIRIDE MC300-1

<400> SEQUENCE: 7

```
Met Val Ser Phe Thr Ser Leu Leu Ala Gly Val Ala Pro Ile Ser Gly
-33         -30                 -25                 -20

Val Leu Ala Ala Pro Ala Ala Glu Val Glu Ser Val Asp Val Glu Lys
            -15                 -10                  -5

Arg Gln Thr Ile Gln Pro Gly Thr Gly Tyr Asn Asn Gly Tyr Phe Tyr
 -1   1              5                  10                  15

Ser Tyr Trp Asn Asp Gly His Gly Gly Val Thr Tyr Thr Asn Gly Pro
                 20                  25                  30

Gly Gly Gln Phe Ser Val Asn Trp Ser Asn Ser Gly Asn Phe Val Gly
                 35                  40                  45

Gly Lys Gly Trp Gln Pro Gly Thr Lys Asn Lys Val Ile Asn Phe Ser
             50                  55                  60

Gly Thr Tyr Asn Pro Asn Gly Asn Ser Tyr Leu Ser Val Tyr Gly Trp
 65                  70                  75

Ser Arg Asn Pro Leu Ile Glu Tyr Tyr Ile Val Glu Asn Phe Gly Thr
 80                  85                  90                  95

Tyr Asn Pro Ser Thr Gly Ala Thr Lys Leu Gly Glu Val Thr Ser Asp
                 100                 105                 110

Gly Ser Val Tyr Asp Ile Tyr Arg Thr Gln Arg Val Asn Gln Pro Ser
                 115                 120                 125

Ile Glu Gly Thr Ser Thr Phe Tyr Gln Tyr Trp Ser Val Arg Arg Thr
                 130                 135                 140

His Arg Ser Ser Gly Ser Val Asn Thr Ala Asn His Phe Asn Ala Trp
             145                 150                 155

Ala Ser His Gly Leu Thr Leu Gly Thr Met Asp Tyr Gln Ile Val Ala
160                 165                 170                 175

Val Glu Gly Tyr Phe Ser Ser Gly Ser Ala Ser Ile Thr Val Ser
                 180                 185                 190
```

<210> SEQ ID NO 8
<211> LENGTH: 822
<212> TYPE: DNA
<213> ORGANISM: TRICHODERMA VIRIDE MC300-1
<220> FEATURE:
<221> NAME/KEY: sig_peptide
<222> LOCATION: (14)..(112)
<220> FEATURE:
<221> NAME/KEY: CDS
<222> LOCATION: (14)..(112)
<220> FEATURE:
<221> NAME/KEY: mat_peptide
<222> LOCATION: (113)..(809)
<220> FEATURE:
<221> NAME/KEY: CDS
<222> LOCATION: (113)..(285)
<220> FEATURE:
<221> NAME/KEY: intron
<222> LOCATION: (286)..(412)
<220> FEATURE:
<221> NAME/KEY: CDS
<222> LOCATION: (413)..(809)

<400> SEQUENCE: 8

```
aggcctgcgc atc atg gtc tcc ttc acc tcc ctc ctc gcc ggc gtc gcg ccc      52
            Met Val Ser Phe Thr Ser Leu Leu Ala Gly Val Ala Pro
```

-continued

```
              -33            -30                  -25
atc tcc gga gtc ttg gcc gct ccc gct gct gag gtc gag tcc gtg gac        100
Ile Ser Gly Val Leu Ala Ala Pro Ala Ala Glu Val Glu Ser Val Asp
        -20             -15                 -10              -5 gtt gaa aag cgc cag acg att cag ccc ggc acg ggc tac aac aac ggc        148
Val Glu Lys Arg Gln Thr Ile Gln Pro Gly Thr Gly Tyr Asn Asn Gly
            -1  1               5                       10 tac ttc tac tcg tac tgg aac gac ggc cac ggc ggc gtg acg tac acc        196
Tyr Phe Tyr Ser Tyr Trp Asn Asp Gly His Gly Gly Val Thr Tyr Thr
            15                  20                  25 aat ggc ccc ggc ggc cag ttc tcc gtc aac tgg tcc aac tcg ggc aac        244
Asn Gly Pro Gly Gly Gln Phe Ser Val Asn Trp Ser Asn Ser Gly Asn
        30              35                  40 ttt gtc ggc ggc aag gga tgg cag ccc ggc acc aag aac aa                 285
Phe Val Gly Gly Lys Gly Trp Gln Pro Gly Thr Lys Asn Lys
        45              50                  55 gtaagactat atacaacccc accttctgac caaacccccct atccaacgac agaatataaa     345
accaagggcg tgattatcat ggagagagag agtgtgtgtg atctaacggt tttgttctga      405 aaacaag g gtc atc aac ttc tcg ggc acc tac aac ccc aac ggc aac          452
          Val Ile Asn Phe Ser Gly Thr Tyr Asn Pro Asn Gly Asn
                60                  65                      70 agc tac ctc tcc gtg tac ggc tgg tcg cgc aac ccc ctg atc gag tac        500
Ser Tyr Leu Ser Val Tyr Gly Trp Ser Arg Asn Pro Leu Ile Glu Tyr
            75                  80                  85 tac atc gtc gag aac ttt ggc acc tac aac ccg tcc acc ggc gcc acc        548
Tyr Ile Val Glu Asn Phe Gly Thr Tyr Asn Pro Ser Thr Gly Ala Thr
        90                  95                      100 aag ctg ggc gag gtg acg tcg gac ggc agc gtc tac gac atc tac cgc        596
Lys Leu Gly Glu Val Thr Ser Asp Gly Ser Val Tyr Asp Ile Tyr Arg
105                 110                 115                 120 acg cag cgc gtc aac cag ccg tcc atc gag ggc acc tcc acc ttt tac        644
Thr Gln Arg Val Asn Gln Pro Ser Ile Glu Gly Thr Ser Thr Phe Tyr
            125                 130                 135 cag tac tgg tcc gtc cgc cgc acc cac cgc tcc agc ggc tcc gtc aac        692
Gln Tyr Trp Ser Val Arg Arg Thr His Arg Ser Ser Gly Ser Val Asn
            140                 145                 150 acg gcg aac cac ttc aac gcg tgg gcc tcg cac ggc ctg acg ctg ggc        740
Thr Ala Asn His Phe Asn Ala Trp Ala Ser His Gly Leu Thr Leu Gly
            155                 160                 165 acc atg gat tac cag att gtt gcc gtg gag ggc tac ttt agc tct ggc        788
Thr Met Asp Tyr Gln Ile Val Ala Val Glu Gly Tyr Phe Ser Ser Gly
        170                 175                 180 tct gct tcc atc acc gtc agc taaggtactc gag                             822
Ser Ala Ser Ile Thr Val Ser
185                 190
```

<210> SEQ ID NO 9
<211> LENGTH: 10
<212> TYPE: PRT
<213> ORGANISM: TRICHODERMA VIRIDE MC300-1

<400> SEQUENCE: 9

```
Ser Ala Xaa Thr Leu Gln Ala Glu Thr His
1               5                   10
```

<210> SEQ ID NO 10
<211> LENGTH: 6
<212> TYPE: PRT
<213> ORGANISM: TRICHODERMA VIRIDE MC300-1

```
<400> SEQUENCE: 10

Glu Phe Ser Phe Asp Val
  1               5

<210> SEQ ID NO 11
<211> LENGTH: 18
<212> TYPE: PRT
<213> ORGANISM: TRICHODERMA VIRIDE MC300-1

<400> SEQUENCE: 11

Glu Thr His Pro Pro Leu Thr Trp Gln Lys Xaa Ser Ser Gly Gly Thr
  1               5                  10                  15

Xaa Thr

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 12
atgtatcaaa agttggcc                                                        18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 13
ttacaagcac tgagagtag                                                       19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 14
tcactttcca gcagcccaac gcc                                                  23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 15
caactctccc aacgccaagg tcg                                                  23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID
```

```
<400> SEQUENCE: 16
cgtcgggtag gtagagtcca gcc                                           23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 17
tctcgaactg agtgacgacg gtc                                           23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 18
ctgccatgtc agaggcgggt gag                                           23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 19
actccaacat caagttcggc ccc                                           23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 20
aactcccact gagcctttac gtc                                           23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 21
caattaagtg gctaaacgta ccg                                           23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 22
```
gcaaaaatat agtcgaatct gcc                                          23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 23
gctggaatgc tcgctagctt ggc                                          23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 24
actgttggag accagcttgt ccg                                          23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 25
cgcagtagga gaatagaaac ccc                                          23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 26
ctgctgtcaa tccccgctac tgg                                          23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 27
ccttcgagaa aaggagattc gcg                                          23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 28
cagctccttg gcaaaagcag tgg                                            23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 29
agatcatcag ttgaggttag acc                                            23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 30
tgtataaaat taggttcggg tcc                                            23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 31
ctactcatca actcagatcc tcc                                            23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 32
ggaagcctca gaagtagata cagc                                           24

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 33
tcgactacgg actgcgcatc                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 34
caagcttttg ccacagtacc                                                20

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 35
gatacatgat gcgcaggcct tagtcgacta gaatgc                                   36

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 36
gatcctcaag cttttgctcg agtaccttac aagcac                                   36

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 37
ggagggtgca tgccgactga gcccgggcag tagcc                                    35

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 38
gccgggagag gatccagtgg agg                                                 23

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 39
gctcgagtac cttactgcag gcactgagag                                          30

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 40
ggggcatgcg ctgatggcaa gtccacccg                                           29

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 41
ggggtcgact accttacagg cactgatggt acc                                    33

<210> SEQ ID NO 42
<211> LENGTH: 10
<212> TYPE: PRT
<213> ORGANISM: TRICHODERMA VIRIDE MC300-1

<400> SEQUENCE: 42

Gln Asp Val Trp Gly Gln Cys Gly Gly Ile
 1               5                  10

<210> SEQ ID NO 43
<211> LENGTH: 11
<212> TYPE: PRT
<213> ORGANISM: TRICHODERMA VIRIDE MC300-1

<400> SEQUENCE: 43

Thr Pro Thr Gly Ser Gly Asn Ser Trp Thr Asp
 1               5                  10

<210> SEQ ID NO 44
<211> LENGTH: 7
<212> TYPE: PRT
<213> ORGANISM: TRICHODERMA VIRIDE MC300-1

<400> SEQUENCE: 44

Ser Thr Tyr Ile Leu Thr Glu
 1               5

<210> SEQ ID NO 45
<211> LENGTH: 15
<212> TYPE: PRT
<213> ORGANISM: TRICHODERMA VIRIDE MC300-1

<400> SEQUENCE: 45

Phe Ala Gly Val Asn Ile Ala Gly Phe Asp Phe Gly Xaa Thr Thr
 1               5                  10                  15

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 46
atgaacaagt ccgtggctc                                                    19

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      NUCLEIC ACID

```
<400> SEQUENCE: 47
ttactttctt gcgagacacg agc                                              23

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 48
gggaggcctg cgcatcatgg ctccattgct gcttgc                                36

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 49
gggctcgagt accttacttc ctggcgagac acgagc                                36

<210> SEQ ID NO 50
<211> LENGTH: 14
<212> TYPE: PRT
<213> ORGANISM: TRICHODERMA VIRIDE MC300-1

<400> SEQUENCE: 50

Gln Thr Ile Gly Pro Gly Thr Gly Phe Asn Asn Gly Tyr Phe
  1               5                  10

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 51
gggaggcctg cgcatcatgg tctccttcac ctccc                                 35

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      NUCLEIC ACID

<400> SEQUENCE: 52
gggctcgagt accttagctg acggtgatgg aagc                                  34
```

REGULATORY SEQUENCE OF CELLULASE CBH1 GENES ORIGINATING IN *TRICHODERMA VIRIDE* AND SYSTEM FOR MASS-PRODUCING PROTEINS OR PEPTIDES THEREWITH

BACKGROUND OF THE INVENTION

1. Field of the Invention

The present invention relates to a high-yield production system for a protein or peptide, and more specifically it relates to a production system using a regulator sequence derived from *Trichoderma viride*, and to a production technique for a protein or peptide which employs the production system.

2. Description of the Related Art

Filamentous fungi are known to secrete significant amounts of extracellular proteins, particular enzymes. For example, the genus Aspergillus secretes amylases, proteases, lipases, cellulases and other enzymes, which are therefore utilized in various different fields. As to their yields, it has been reported, for example, that *Aspergillus niger* produces over 20 g of glucoamylase per liter of liquid culture, while *Aspergillus oryzae* produces about 50 g per kilogram of solid culture (Katuya Gomi: Kagaku to Seibutsu (1994), 32, 269).

Recent years have brought an accumulation of knowledge regarding production techniques for target proteins utilizing the protein-producing abilities of these filamentous fungi. Examples of filamentous fungi-derived foreign proteins which have been produced include Mucor miehei-derived rennin in *Aspergillus nidulans* hosts (G. L. Gray, et al.; Gene (1986), 48, 41), *Aspergillus ficuum*-derived phytase in *Aspergillus niger* hosts (R. F. M. van Gorcom, et al.: European Patent Application (1991), 0420358A1), *Mucor miehei*-derived rennin (T. Christensen, et al.: Bio/Technology (1988), 6, 1419) and lipase (B. Huge-Jensen, et al.: Lipids (1989), 24, 781) in *Aspergillus oryzae* hosts, *Phlebia radiata*-derived laccase in *Trichoderma reesei* hosts (M. Saloheimo, et al.: Bio/Technology (1991), 9, 987), *Aspergillus oryzae*-derived α-amylase in *Trichoderma viride* hosts (C. Cheng, et al.: Agric. Biol. Chem. (1991), 55, 1817) and Fusarium genus-derived alkali proteases in *Acremonium chrysogenum* hosts (Shigeru Morita, et al.: Summary of Meeting Lectures of the Nihon Nogei Kagakukai (1993), p.140). Production of human, bovine and other animal proteins as well as plant proteins has also been confirmed in *Aspergillus nidulans, Aspergillus niger, Aspergillus oryzae* and *Trichoderma reesei* hosts.

Thus, filamentous fungi are clearly excellent as production hosts for proteins and polypeptides. The productivity of the target protein also becomes an important issue in terms of industrial applications. The factors considered to be important in determining productivity include (1) regulation for effective and high-yield transcription and translation of the target protein by a regulator region (for example, promoter and terminator) which is capable of expression in the host, (2) a translation product with the desired higher-order structure (activity type) and (3) stable extracellular secretion of the same. To this end there have been developed many effective promoters, such as the Aspergillus amylase gene promoter and the Trichoderma cellulase gene promoter. It is currently known that the use of an α-amylase gene promoter in an *Aspergillus oryzae* host can produce 3.3 g of *Mucor miehei* rennin per liter of liquid culture.

No matter how powerful the promoter, however, it is usually not possible to obtain the target protein in an amount exceeding the protein yield of the host. In fact, only 30% protein productivity is achieved in the case of *Aspergillus oryzae* mentioned above. This is thought to be due to the fact that the gene which is used remains in the host, that the codon use frequency in the translated region differs among species, that the secretion mechanism differs among species, and other reasons as well, but as yet no technique has been discovered to solve these problems.

It has therefore been considered that target protein yields could be enhanced by improving the protein production of the hosts themselves.

Filamentous fungi belonging to the genus Trichoderma are known to be excellent cellulase producing cells. In particular, *Trichoderma reesei* has been widely studied in terms of its foreign protein production, and much research is being conducted on foreign protein expression using a promoter for the cellobiohydrolase 1 (cbh1) gene, said to constitute about 70% of the secreted protein of that species (Uusitalo J M., et al.: J. Biotechnol. (1991), 17, 35. Joutsjoki V V., et al.: Curr. Genet. (1993), 24, 223. Barnett C C., et al.: Biotechnology (1991), 9, 562. Berges T., et al.: Curr. Genet. (1993), 24, 53. Saloheimo M., et al.: Gene (1989), 85, 343. Saarelainen R., et al.: Mol. Gen. Genet. (1993), 241, 497). However, only C. Cheng et al. have reported a foreign protein expression system using *Trichoderma viride* as the host. According to C. Cheng et al., the α-amylase gene was introduced into a protease-deficient strain of *Trichoderma viride* as the host using the cbh1 promoter and signal sequence, to produce α-amylase at 1 g per liter of liquid culture. While this demonstrates that foreign protein production is possible with *Trichoderma viride*, that production level is not satisfactory in terms of cost on a practical production scale.

SUMMARY OF THE INVENTION

The present inventors have now found that a cellulase gene regulator sequence derived from *Trichoderma viride* gives high expression of target proteins and have subsequently succeeded in using this regulator sequence to produce *Humicola insolens*-derived endoglucanase at 15 g/L. Such productivity has not been achieved in any foreign protein production system of filamentous fungi disclosed to date. The present invention has been accomplished on the basis of this finding.

It is therefore an object of the present invention to provide a regulator sequence which gives high expression of target proteins and a high yield production system for proteins which employs the sequence.

It is a further object of the invention to provide a method for high-yield production of proteins or peptides using this production system.

The regulator sequence of the invention which gives high expression of target proteins is a regulator sequence of the cellulase cbh1 gene derived from *Trichoderma viride*.

The high-yield production system for proteins according to the invention utilizes this *Trichoderma viride*-derived cellulase cbh1 gene regulator sequence.

BRIEF DESCRIPTION OF THE DRAWINGS

FIG. 4 is a restriction map for plasmid pCB1-M2XR.

DESCRIPTION OF THE PREFERRED EMBODIMENT

Deposit of microorganisms

Figure 2:
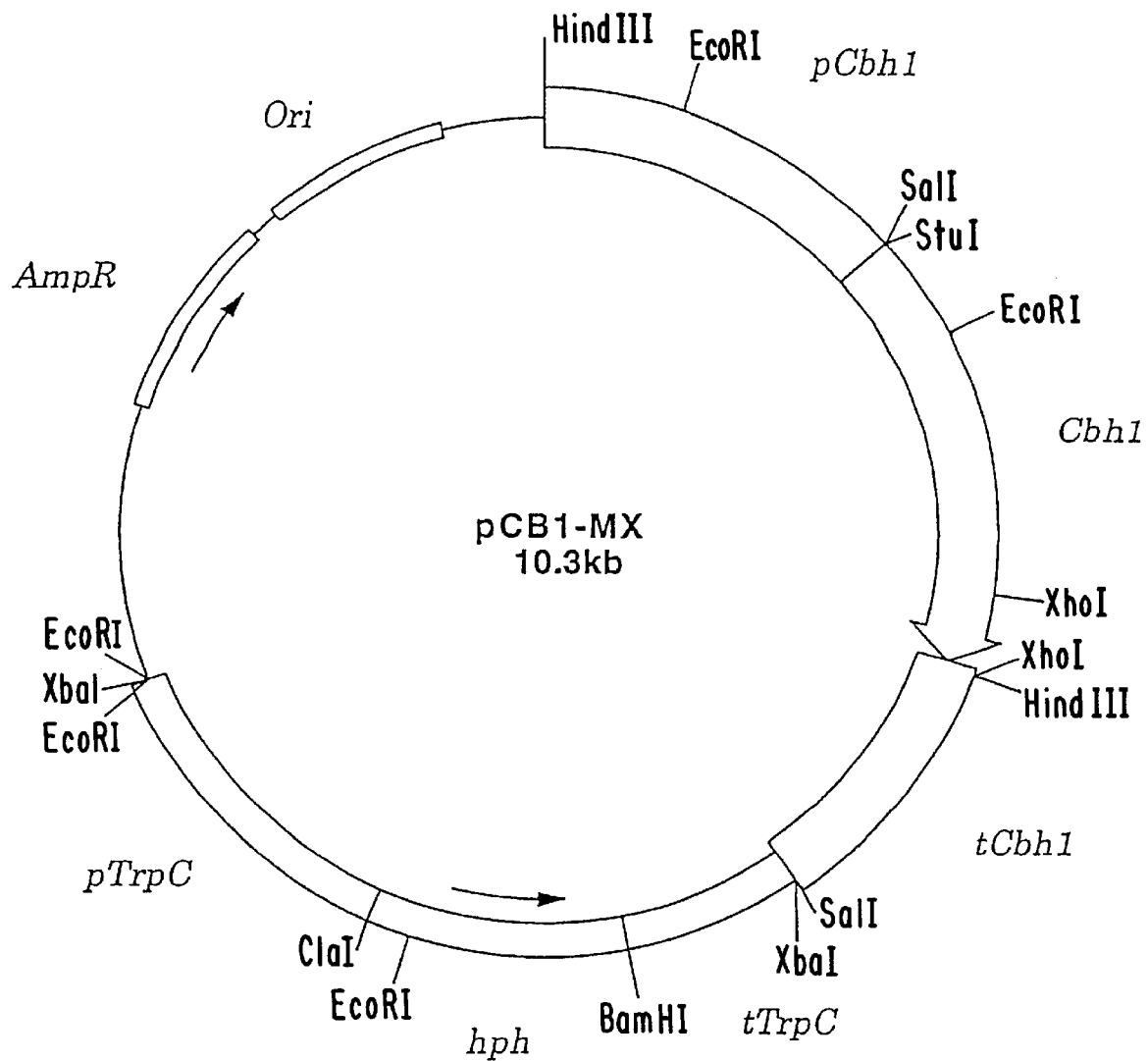
FIG. 2 is a restriction map for plasmid pCB1-MX.

*E. coli* JM109 transformed with plasmid pCB1-MX shown in the map of FIG. 2 was deposited at the National Institute of Bioscience and Human Technology of the Ministry of International Trade and Industry (1-1-3 Higashi, Tsukuba-Shi, Ibaraki-Ken, Japan, hereunder "NIBH") on Sep. 9, 1996 (original depositing date) as FERM BP-6044.

*E. coli* JM109 transformed with plasmid pCB1-M2XR shown in the map of FIG. 4 was deposited at the NIBH on Sep. 9, 1996 (original depositing date) as FERM BP-6045.

Figure 5:
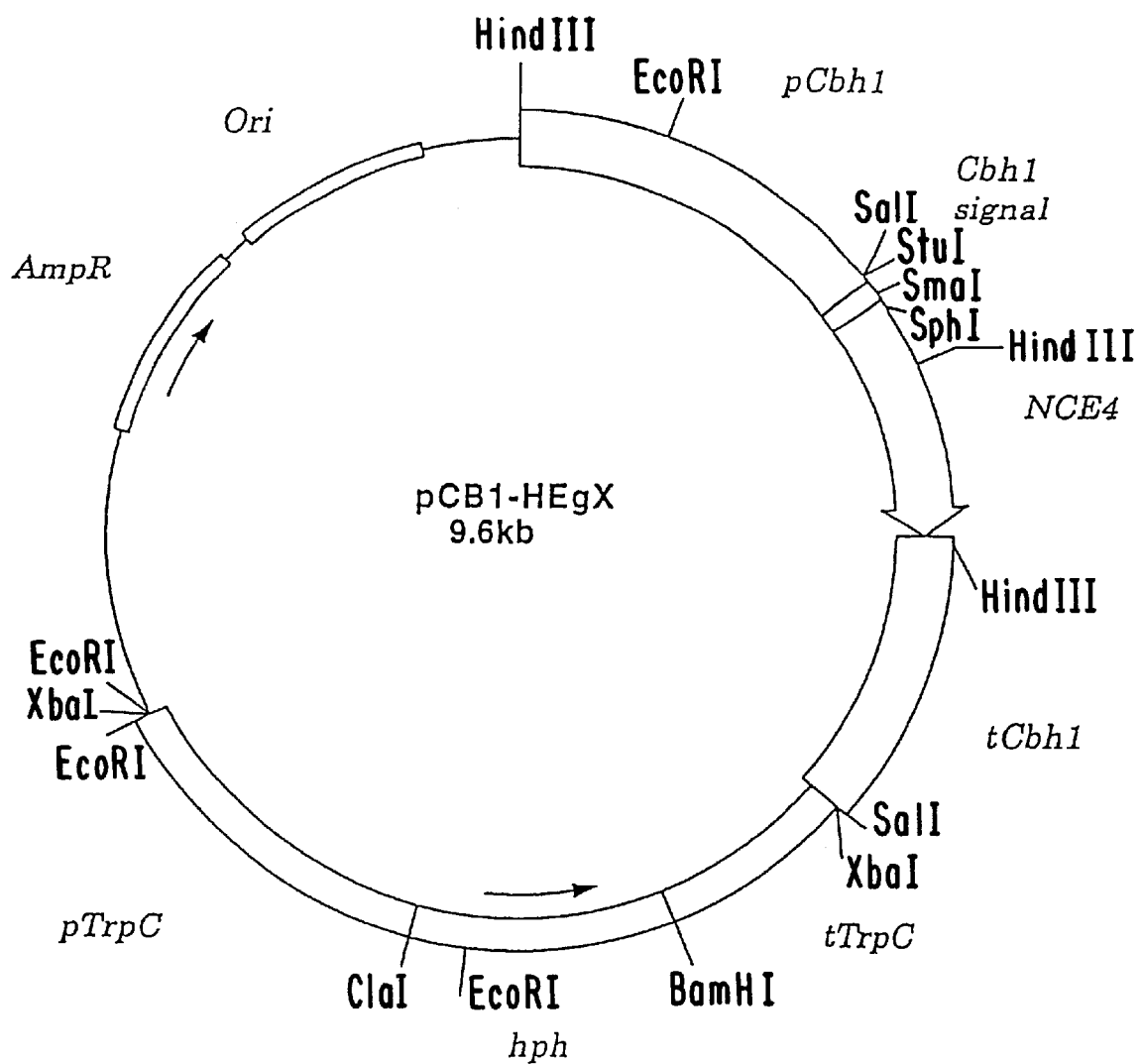
FIG. 5 is a restriction map for plasmid pCB1-HEgX.

*E. coli* JM109 transformed with plasmid pCB1-HEgX shown in the map of FIG. 5 was deposited at the NIBH on Sep. 9, 1996 (original depositing date) as FERM BP-6046.

Figure 6:
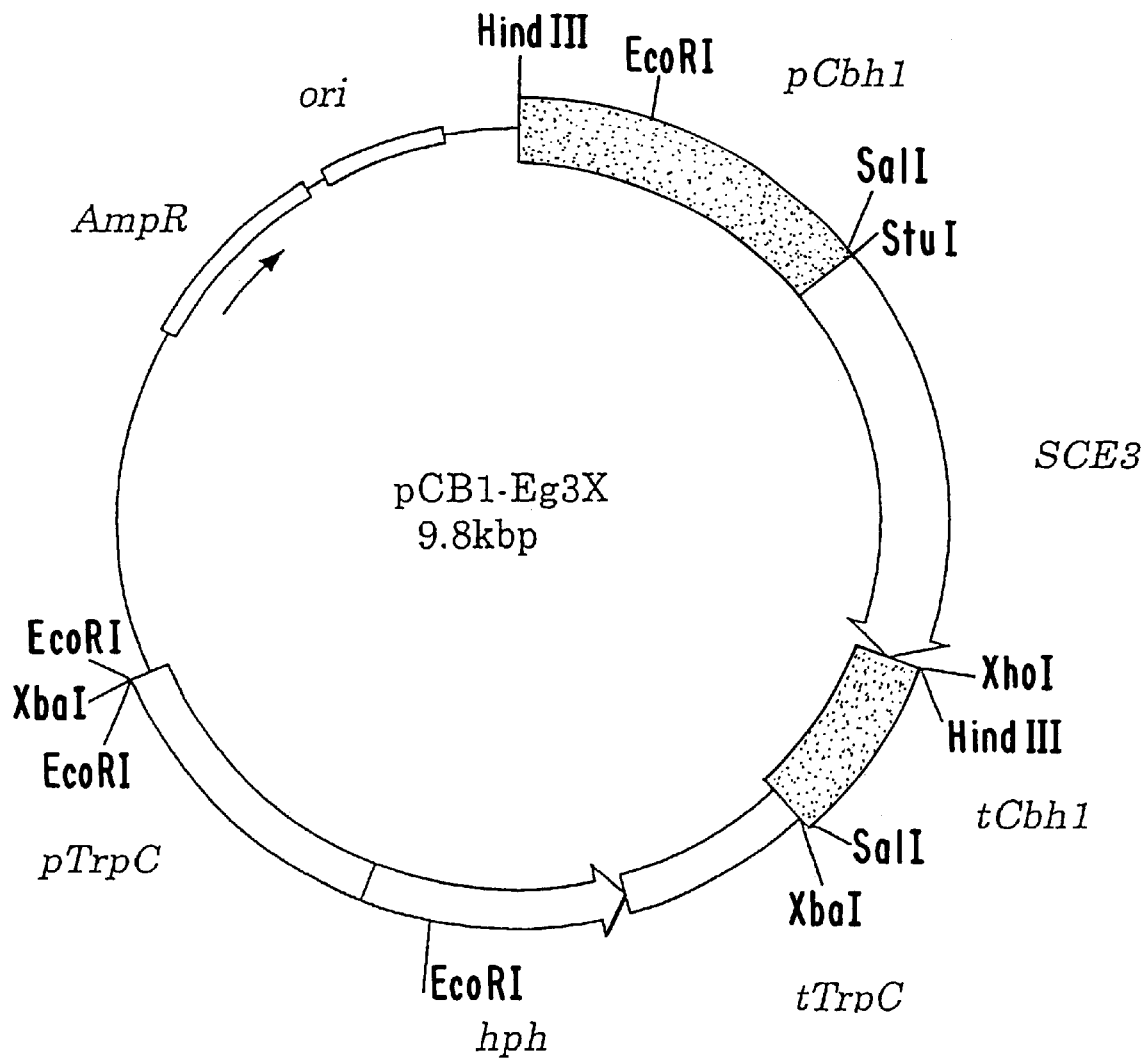
FIG. 6 is a restriction map for plasmid pCB1-Eg3X.

*E. coli* transformed with plasmid pCB1-Eg3X shown in the map of FIG. 6 was deposited at the NIBH on Aug. 11, 1997 as FERM BP-6043.

Figure 7:
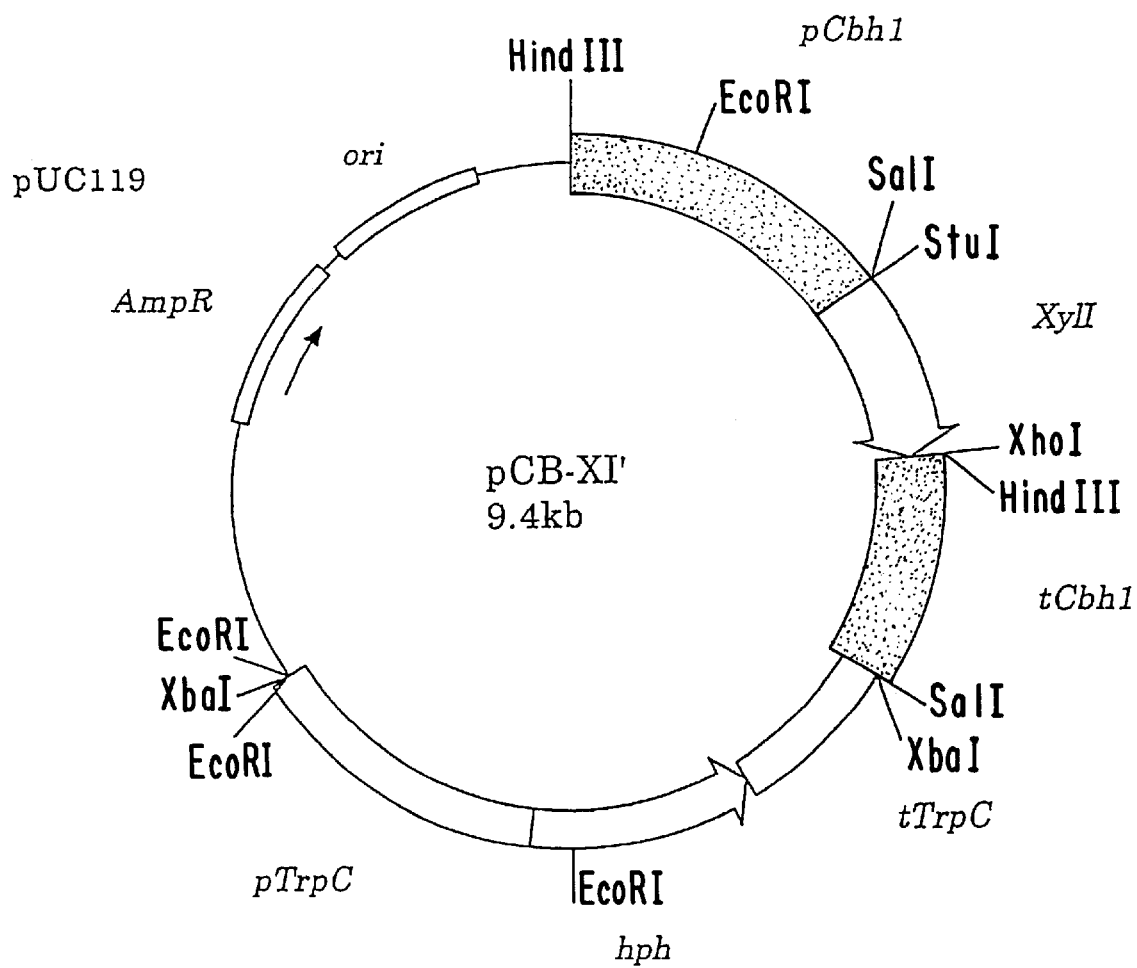
FIG. 7 is a restriction map for plasmid pCB-XI'.

*E. coli* transformed with plasmid pCB-XII shown in the map of FIG. 7 was deposited at the NIBH on Aug. 11, 1997 as FERM BP-6042.

*Trichoderma viride* MC300-1 from which the cbh1 gene and its regulator sequence according to the invention were derived was deposited at the NIBH on Sep. 9, 1996 (original depositing date) as FERM BP-6047.

Definitions

The terms "protein" and "peptide" are herein used synonymously unless otherwise noted. The term "modified sequence" as used herein is intended to mean a DNA sequence or amino acid sequence with an insertion, substitution or deletion of a certain number (for example, one or a few) bases or amino acids, or additions at either or both terminals thereof.

*Trichoderma viride*-derived cellulase cbh1 gene regulator sequence

The regulator sequence of the present invention is a regulator sequence derived from *Trichoderma viride*. According to the present invention, a regulator sequence refers to at least one selected from the group consisting of promoters, signal sequences and terminators.

Figure 1:
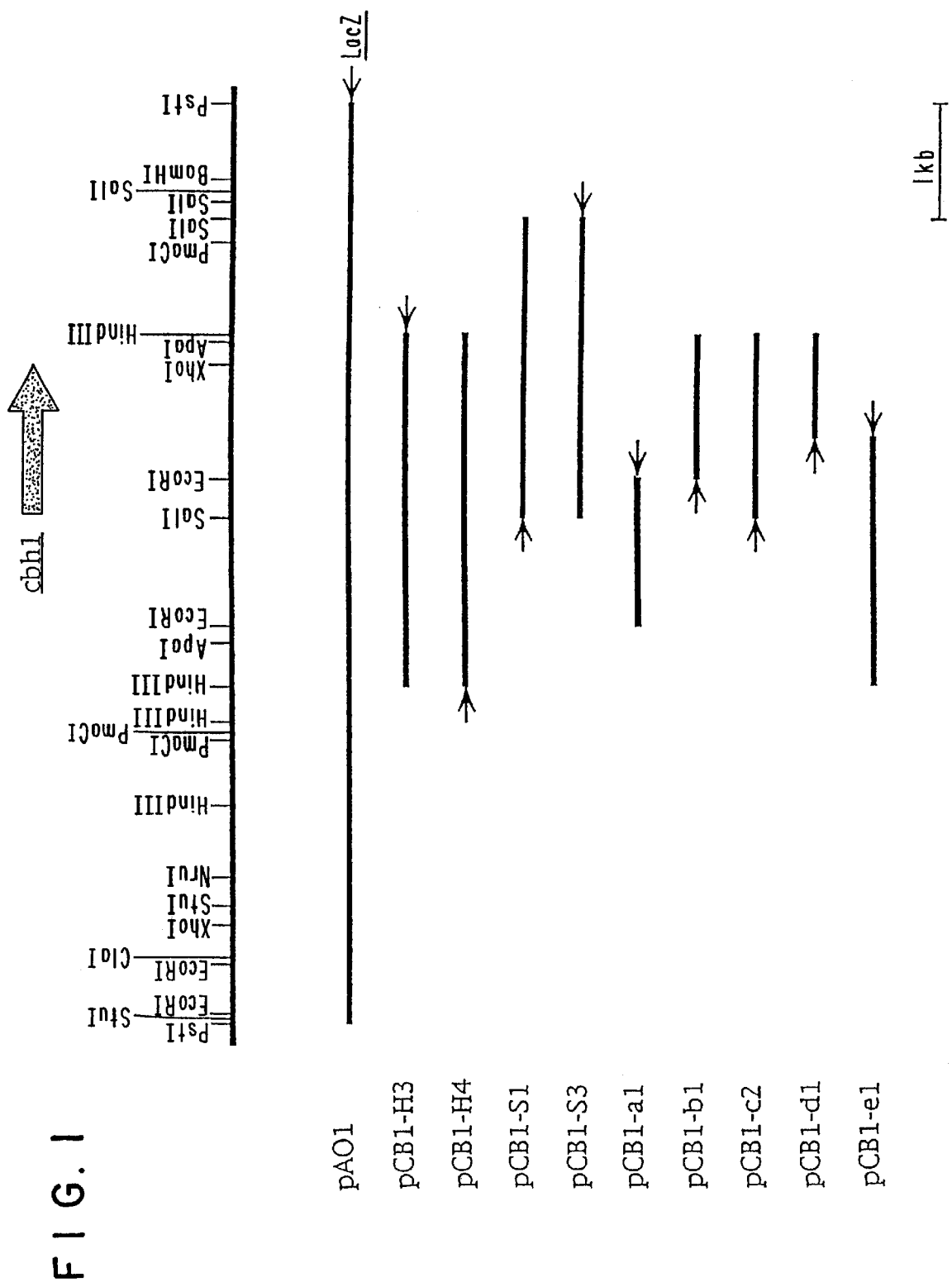
FIG. 1 is a restriction map for the *Trichoderma viride*-derived cellulase cbh1 gene and plasmid pA01 containing its regulator sequence, as well as for plasmids pCB1-H3, pCB1-H4, pCB1-S1, pCB1-S3, pCB1-a1, pCB1-b1, pCB1-c2, pCB1-d1 and pCB1-e1 with its cloned digestion fragments.

The regulator sequence of the present invention is, more specifically, a regulator sequence for the cbh1 gene in plasmid pA01 shown in FIG. 1.

A preferred promoter sequence according to the present invention comprises a sequence in the region from the N-terminal of the cbh1 gene to about 1.5 kb upstream in plasmid pA01 shown in FIG. 1, for example the sequence from the N-terminal of the cbh1 gene to the upstream HindIII site on plasmid pA01.

The promoter sequence of the present invention includes not only the full sequence of this region but also modified sequences thereof which retain high promoter activity. In the present invention, high promoter activity is a strong promoter activity which results in high expression of the cellulase NCE4 gene described hereunder, and more specifically it refers to promoter activity which results in expression of NCE4 to 7–8 g, and preferably 15 g or more, per liter of medium. Given the descriptions and deposited strains in the examples which follow and the sequence listed as SEQ.ID. No.1, a person skilled in the art could easily predict the existence of such modified sequences and could easily produce them.

A preferred signal sequence according to the present invention is the DNA sequence coding for amino acids −17 to −1 of SEQ.ID. No.1. The invention also encompasses modified sequences of this DNA sequence which code for amino acid sequences retaining signal sequence activity. For such modified sequences as well, given the descriptions and deposited strains in the examples which follow and the sequence listed as SEQ.ID. No.1, a person skilled in the art could easily predict the existence of such modified sequences and could easily produce them.

Incidentally, it would be readily apparent to a person skilled in the art in actually utilizing these sequences, that a few amino acids could be added to the N-terminal of the cbh1 protein in addition to the aforementioned signal sequence. That is, in utilizing these signal sequences, the target protein may be obtained as a fused protein with a peptide consisting of a few of the N-terminal amino acids of the cbh1 protein, or as a fused protein with the cbh1 protein.

As preferred terminator sequences according to the present invention comprises a sequence in the region from the C-terminal of the cbh1 gene to about 1 kb downstream in plasmid pA01, for example the sequence from the C-terminal of the cbh1 gene to the downstream SalI site, on plasmid pA01.

The terminator sequence of the present invention encompasses not only the full sequence of this region but also modified sequences which retain the terminator activity.

These regulator sequences, and especially the promoter sequence, express the cellulase NCE4 gene described hereunder at a very high efficiency. Thus, according to a preferred embodiment of the present invention there is provided a regulator sequence which is preferably used for expression of the NCE4 gene, and especially a promoter sequence which is preferably used for expression of the NCE4 gene. According to this preferred embodiment of the present invention, a productivity of 7–8 g, and preferably about 15 g of cellulase NCE4 is achieved per liter of liquid culture.

Expression Vector and Host

According to the present invention there is also provided an expression vector for expression of target proteins using the regulator sequence above.

The expression vector of the present invention, according to the first embodiment, comprises the regulator sequence and in some cases a gene marker. The expression vector of the present invention also comprises a DNA sequence coding for a target protein which is operably linked to the regulator sequence in addition to the expression vector according to the first embodiment. Thus, expression vectors which comprise at least one selected from the group consisting of promoters, signal sequences and terminators according to the present invention are also within the scope of the present invention.

As mentioned above, the promoter sequence of the present invention is a highly useful one. Therefore, according to the preferred embodiment of the present invention, there is provided an expression vector which includes at least a promoter sequence according to the present invention. The signal sequence and terminator sequence in the expression vector may be ones other than signal and terminator sequences according to the present invention, but it is preferred to use the signal sequence and terminator sequence according to the I-present invention. Examples of such vectors include the expression vectors pCB1-MX and pCB1-M2XR constructed in the examples given below.

The expression vector of the present invention preferably has the basic construction of a vector, for example a plasmid, which is replicable in the host cells used to construct the expression vector. As such vectors there may be mentioned the *E. coli* replicable vectors, puC vector, pTV vector, pBluescript, pBR322, etc. The method for constructing the vector of the present invention may be any method commonly employed in the field of gene recombination.

The gene marker may be appropriately selected depending on the method of selection of the transformants. For example, a gene coding for drug resistance or an auxotroph compensation gene may be used. There are no particular restrictions on the drug resistant gene which may be used according to the present invention which are for drugs to which the host cells exhibit sensitivity. For example when *Trichoderma viride* is used as the host, it is preferred to use a destomycin resistant gene derived from *Streptomyces rimofaciens*, a hygromycin B resistant gene derived from *E. coli* or a bleomycin resistant gene derived from *Streptococcus hindustanus*.

According to a preferred embodiment of the present invention, the promoter and terminator for the trpC gene derived from *Aspergillus nidulans* (Mullaney, E. J. et al., Mol. Gen. Genet. 199: 37–45, 1985) are obtained by a publicly known method, and used to prepare a cassette which allows expression of the hygromycin B resistant gene (Cullen, D. et al., Gene (1987), 57, 21).

The expression vector of the present invention can be used for expressed production of different target proteins or peptides. According to the present invention, target proteins or peptides are not only "exogenous proteins" which are not present in the host cells, but also proteins which are expressed in the host cells albeit in trace amounts. Genes coding for target proteins in expression vectors according to the present invention include genes coding for industrially useful proteins such as cellulases, amylases, lipases, proteases and phytases. Artificial modifications of these genes can also be used as genes coding for target proteins.

The expression vector of the present invention is not particularly restricted so long as it allows expression of the *Trichoderma viride*-derived cbh1 gene in the host cells. It is preferably an expression system in combination with a microorganism belonging to the genus Trichoderma as the host. According to a preferred embodiment of the present invention, *Trichoderma viride* is utilized as the microorganism belonging to the genus Trichoderma.

According to another preferred embodiment of the present invention, the high-yield cellulase-producing strain *Trichoderma viride* MC300-1 is used as the most preferred *Trichoderma viride* host.

According to a preferred embodiment of the present invention, *Trichoderma reesei* may also be used as the host cells.

According to a preferred embodiment of the present invention, the expression system of the present invention can be very advantageously used for expression of cellulases. Specific examples of cellulases include the cellulase NCE4 of *Humicola insolens* and its modified proteins as well as the 43 kD endoglucanase described in WO91/17243 (Japanese Patent Laid-Open No. 509223/1993), the endoglucanase SCE3 of *Trichoderma viride* and its modified proteins, and the xylanase SXY1 of *Trichoderma viride* and its modified proteins. The cellulase NCE4 derived from *Humicola insolens* is a protein having the sequence from Nos. 1 to 284 of SEQ.ID. No.3. The endoglucanase SCE3 is a protein having the sequence from Nos. 1 to 397 of SEQ.ID. No.5. The xylanase SXY1 derived from *Trichoderma viride* is a protein having the sequence from Nos. 1 to 190 of SEQ.ID. No.7.

The term "modified proteins" is used to refer to proteins having modifications of the amino acid sequences of the aforementioned proteins, including a certain number (for example, one or a few) amino acid additions, insertions, eliminations, deletions or substitutions, which proteins still maintain the original enzyme activity, especially endoglucanase activity or endoxylanase activity.

According to a preferred embodiment of the present invention, the expression vector pCB1-HEgX constructed in the examples which follow may be mentioned as a preferred vector in an expression system for cellulase NCE4. As preferred vectors in expression systems for endoglucanase SCE3 or xylanase SXY1 there may be mentioned the expression vectors pCB1-Eg3X and pCB-XI' constructed in the examples which follow.

Production of Target Protein

The production of a target protein according to the present invention may be accomplished by culturing host cells transformed with an expression vector according to the present invention as described above in an appropriate medium, and collecting the target protein or peptide from the culture.

According to a preferred embodiment of the present invention there is provided a very high efficiency production system for target proteins. In the case of *Trichoderma viride* host cells, for example, it is possible to produce target proteins at 7 g or 8 g or more, and preferably 15 g or more, per liter of liquid culture. Such amounts are very high compared to conventionally known protein expression systems. This shows that the target protein expression system of the present invention offers a very high degree of usefulness.

Higher yields can be achieved when the target protein is cellulase NCE4, for example, which is an enzyme with very high intrinsic activity. The resulting advantages include efficient production of cellulase preparations which are useful for nap removal and weight reduction of cellulose-containing fibers, and decoloration of denim dyed cellulose-containing fibers.

In the production method for a target protein according to the present invention, the culturing of the transformants may be carried out by a culturing method under aerobic conditions, a shake culture method, electric spinner culturing method or deep culture method, in a medium containing common components such as carbon sources, nitrogen sources, inorganic salts and growth factor components. The pH of the medium may be, for example, about 4–8. In the case of *Trichoderma viride* host cells, the culturing may be carried out under normal conditions commonly used for culturing of *Trichoderma viride*; for example, a temperature of 20° C.–37° C., and preferably 26° C.–28° C., with a culturing time of about 48–168 hours.

The recovery of the protein or peptide of the present invention from the culture can be accomplished by any one or appropriate combination of common separating means which take advantage of its properties, for example, solvent extraction, ion-exchange resin methods, adsorption or distribution column chromatography, gel filtration, dialysis, precipitation, etc.

Cellulase cbh1 and its Gene

The cellulase cbh1 gene derived with the regulator sequence of the present invention includes part or the entirety of the sequence of SEQ.ID. No.1. The invention further encompasses its modified sequences, i.e. *Trichoderma viride*-derived cbh1 fragments of SEQ.ID. No.1 which have been modified with additions, insertions, deletions or substitutions in the structure of the basic gene (promoter, signal sequence, terminator, etc.) or the structure of the translated region (core site, linker site, substrate-binding site) using common gene engineering methods (such as site-directed mutation).

The DNA sequence of SEQ.ID. No.1 represents the DNA sequence of the chb1 gene derived from *Trichoderma viride* chromosome. The DNA sequence of SEQ.ID. No.1 has an open reading frame which begins with ATG at sequence position 1438 and ends with the termination codon (TAA) at sequence position 3109. The DNA sequence from sequence positions 1489–3108 corresponds to the mature cbh1 protein consisting of 497 residues. In addition, two introns were confirmed to be present in the DNA sequence of SEQ.ID. No.1.

The cbh1 gene of the present invention has not been identified as identical to any cellulase gene which has been cloned to date and whose DNA sequence has been elucidated. Specifically, it has already been identified in comparison to the cellulase genes registered in the DNA data base: GenBank R96, August, 1996.

The cbh1 protein of SEQ.ID. No. 2, also, has not been identified as identical to any cellulase gene which has been cloned to date and whose DNA sequence has been elucidated. Specifically, it has already been identified in comparison to the cellulase proteins registered in the amino acid data base: Protein Identification Resource R48 March, 1996, SWISS-PROT R33 February, 1996.

Given the amino acid sequence of a protein, a DNA sequence coding therefor can be easily determined, and many different DNA sequences coding for all or part of the amino acid sequence of SEQ.ID. No.1 can be selected. Thus, a sequence coding for part or all of the amino acid sequence of SEQ.ID. No.1 according to the present invention refers to any sequence coding for part or all of the amino acid sequence of SEQ.ID. No.2, i.e. sequences coding for those same amino acids and having degenerately-related codons in their DNA sequences.

The DNA of the present invention may be naturally-derived or totally synthetic as well as synthesized one utilizing a part of a naturally derived sequence. As typical methods for obtaining DNA there may be mentioned methods commonly employed in the field of genetic engineering, such as a method by screening from a chromosome library of *Trichoderma viride* using a suitable DNA probe constructed based on information of the partial amino acid sequence. It may also be obtained from the deposited strain.

The sequence of the cbh1 gene according to the present invention clearly shows a difference between *Trichoderma viride* and *Trichoderma reesei*. That is, while homology between the DNA sequences of the cbh1 translated regions is approximately 96%, the homology in the non-translated regions (introns) is only 66%, and the DNA sequences of the promoter and terminator show no homology at their respective distances of 150 bp and 170 bp and greater from the translated regions. This indicates that despite the same origin for the cbh1 genes, the genetic variety among successive strains is considerably wide.

It has been traditionally common to classify filamentous fungi on the basis of their morphological characteristics, but in recent years, widely employed DNA analysis has been used to confirm differences between strains. For example, differences in the hybridization patterns of *Trichoderma reesei* and *Trichoderma longibrachiatum* cellobiohydrolase (cbh)2 genes have been demonstrated by Southern analysis (Meyer, W., et al.: Curr. Genet. (1992), 21, 27. Morawez, R., et al.: Curr. Genet. (1992), 21, 31).

EXAMPLES

Example 1

Cloning of cbh1 Gene (1a) Purification of cbh1 protein

*Trichoderma viride* MC300-1 was cultured in P medium (1.0% glucose, 4.0% lactose, 2.0% soybean cake, 1.0% yeast extract, 0.5% potassium phosphate, 0.2% ammonium sulfate, 0.2% calcium carbonate, 0.03% magnesium sulfate) for 5 days at 28° C. The liquid culture was centrifuged to remove the cell residue, the culture supernatant was fractionated using an FPLC apparatus by Pharmacia Biotech Co. (RESOURCE Q, 50 mM Tris-HCl (pH 7.8), 0.0–1 M sodium chloride gradient), and the peak eluting at approximately 280 mM sodium chloride concentration was separated off. When this fraction was subjected to SDS-PAGE (SDS-PAGE mini, 8% gel, Tefco Co.), an essentially single band was obtained for cbh1 with a molecular weight of approximately 67 kilodaltons (KDa) by Coomassie brilliant blue R250 dyeing.

(1b) cbh1 Protein Amino Acid Sequence Analysis

The amino acid sequence was analyzed from the amino terminal by the method of Podell, D. N. et al. (Podell, D. N. et al., Biochem. Biophys. Res. Commun. (1978) 81:176), removing the modifying amino terminal residues. Specifically, the purified cbh1 fraction described above was desalted and concentrated, and then prepared to a concentration of about 0.5 μg/μl. This was reacted with pyroglutamate aminopeptidase (sequence grade) by Behrlinger-Mannheim Co. in 0.1 M phosphoric acid buffer as solution (pH 8.0) containing 5 mM dithiothreitol, 10 mM EDTA and 5% glycerol at 50° C. for 6 hours to remove the modifying amino terminal residues. It was then subjected to SDS-PAGE, blotted with a PVDF membrane (Immobilon PSQ, product of Millipore Co.) and then water washed and air dried.

The amino acid sequence of this blot was analyzed using a Perkin-Elmer Protein Sequencer Model 492. The following N-terminal amino acid sequence (10 residues) was decoded as a result.

N-terminal amino acid sequence: Ser-Ala-Xaa-Thr-Leu-Gln-Ala-Glu-Thr-His (SEQ.ID. No.9)

(1c) Peptide Map

The purified cbh1 fraction obtained in Example 1 (1a) above was digested with a 1/50 molar amount of V8 protease (Sigma Co.) in a 100 mM ammonium bicarbonate solution (pH 7.8), and subjected to column chromatography in a Perkin-Elmer Model 172 Preparative HPLC System (column: RP-300 Aquapore C8, 220×2.1 mm, 0.1% trifluoroacetic acid-0.085% trifluoroacetic acid/35% acetonitrile gradient). The two proteins thus obtained were designated as V8-33 and V8-34.

Analysis of their amino acid sequences gave the following sequences.

V8-33: Glu-Phe-Ser-Phe-Asp-Val (SEQ.ID. No.10)

V8-34: Glu-Thr-His-Pro-Pro-Leu-Thr-Trp-Gln-Lys-Xaa-Ser-Ser-Gly-Gly-Thr-Xaa-Thr (SEQ.ID. No.11)

These sequences showed homology with the amino acid sequence of cbh1 protein obtained from *Trichoderma reesei* (S. Shoemaker et al., Bio/Technology (1983), 1, 691). Because they also showed homology with the amino acid sequence of exo-cellobiohydrolase obtained from *Trichoderma viride* (Cheng Cheng et al., Nucleic Acids Res., (1990) 18, 5559), the translated region of the exo-cellobiohydrolase gene derived from *Trichoderma viride* was amplified by PCR and used as a probe for cloning of a gene coding for the same protein. (1d) Amplification of cbh1 Translated Region The cbh1 translated region was amplified by PCR using a genomic DNA of *Trichoderma viride* MC300-1 as the template.

The genomic DNA was isolated by the method of Horiuchi et al. (Hiroyuki Horiuchi et al., J. Bacteriol (1988) 170, 272–278). First, *Trichoderma viride* MC300-1 was cultured for 24 hours in S medium (3.0% glucose, 0.1% polypeptone, 1% yeast extract, 0.14% ammonium sulfate, 0.2% potassium phosphate, 0.03% magnesium sulfate, pH 6.8), and the cells were collected by centrifugation (3500 rpm, 10 minutes). The cells were lyophilized and then suspended in a TE buffer solution (10 mM Tris-HCl, 1 mM EDTA), treated in 3% SDS solution at 60° C. for 30 minutes, and then subjected to TE-saturated phenol extraction to remove the cell residue. After ethanol precipitation of the extract, it was treated with Ribonuclease A (Sigma Co.) and Proteinase K (Wako Pure Chemicals Co.), and then subjected to the cesium chloride density gradient sedimentation equilibrium method with a 65P-7 centrifuge by Hitachi Koki Co. to obtain the DNA.

The PCR was carried out with Takara Taq by Takara Shuzo Co. Using cbh1-N and cbh1-C listed below as primers, and reaction was conducted by repeating 40 cycles of one minute at 94° C., 2 minutes at 50° C. and 3 minutes at 72° C. An approximately 1.7 kbp DNA fragment was amplified as a result. The sequences of cbh1-N and cbh1-C were as follows.

```
                                        (SEQ.ID. No.12)
cbh1-N: 5'-ATG TAT CAA AAG TTG GCC-3'

(SEQ.ID. No.13)
cbh1-C: 5'-TTA CAA GCA CTG AGA GTA G-3'
```

After agarose electrophoresis of the PCR-amplified fragment, it was recovered from the agarose with a Band Prep Kit by Pharmacia Co., and used as a probe for screening.

Example 2

Preparation of *Trichoderma viride* Genomic DNA Library

*Trichoderma viride* MC300-1 genomic DNA was partially digested with Sau3AI. The product was ligated to the BamHI arm of a phage vector, λMBL3 cloning kit (product of Stratagene Co.) using T4 ligase (Ligation Kit Ver.2, product of Takara Shuzo Co.). After ethanol precipitation, it was dissolved in a TE buffer solution. The entire ligated mixture was used to form phage particles with a Gigapack II Packaging Kit by Stratagene Co. The phage was used to infect *E. coli* LE392. The $1.1 \times 10^4$ cell phage library obtained by this method was used for cloning of the target gene.

Example 3

Subcloning of cbh1 Gene (3a) Screening by Plaque Hybridization

An approximately 1.7 kb DNA fragment from the translated region of the exo-cellobiohydrolase gene of *Trichoderma viride* was labeled in advance with an Amersham ECL Direct System.

The phage plaque prepared in Example 2 was transferred to a Hibond N+ nylon transfer membrane (Amersham Co.), and after alkali denaturation was washed with 5-fold concentration SSC (SSC: 15 mM trisodium citrate, 150 mM sodium chloride), and dried to immobilize the DNA. The kit protocol was followed for one hour of prehybridization (42° C.), followed by addition of the previously labeled probe and hybridization for 4 hours (42° C.). The probe was washed according to the kit protocol.

The nylon membrane used for washing of the probe was immersed for one minute in the included detection solution, and was then photosensitized on a Hyperfilm ECL by the same company to obtain 4 positive clones.

(3b) Preparation of Phage DNA

DNA was prepared from the positive clones by the method of Maniatis et al. (J. Sambrook, E. F. Fritsch and T. Maniatis, "Molecular Cloning", Cold Spring Harbor Laboratory Press, 1989).

The host used was *E. coli* LE392. First, LE392 was cultured overnight in LB-MM medium (1% peptone, 0.5% yeast extract, 0.5% sodium chloride, 10 mM magnesium sulfate, 0.2% maltose), and then infected with a phage solution derived from a single plaque, and again cultured overnight in LB-MM medium. To this there were added sodium chloride to 1 M and chloroform to 0.8% to promote lysis of *E. coli*. The cell residue was removed by centrifugation, and the phage particles were recovered from polyethylene glycol (PEG) precipitation (10% PEG6000). The phage particles were digested with Proteinase K in the presence of SDS, and after phenol treatment and ethanol precipitation, the phage DNA was recovered.

The DNA recovered in this manner was subjected to Southern blot analysis with an Amersham ECL Direct System. Upon hybridization using the PCR-amplified fragment of Example 1 as the probe, the same hybridization pattern occurred with a 7 kbp PstI digestion fragment (FIG. 1).

The same hybridization pattern PstI fragment was subcloned in pUC118 (Takara Shuzo Co.) to obtain plasmid pA01.

Example 4

Determination of cbh1 Gene DNA Sequence (4a) Genomic DNA DNA Sequence Analysis

The DNA sequence was determined in the following fashion. The DNA sequence analyzer used was an A.L.F. DNA Sequencer II by Pharmacia Biotech Co. The sequencing gel used was an acrylamide gel commercially available as Hydrolink Long Ranger by FMC Co. The gel forming reagents used (N,N,N',N'-tetramethylethylenediamine, urea, ammonium persulfate) were A.L.F. grade reagents by Pharmacia Biotech Co.

The DNA sequencing reaction was carried out using an Autoread Sequencing Kit by Pharmacia Biotech Co. The gel preparation conditions, sequencing reaction conditions and electrophoresis conditions were set with reference to the respective protocol manuals.

A template plasmid (hereunder referred to as "template") for DNA sequencing was prepared as a template from the following single-stranded DNA and fragment clone.

First, M13 single-stranded DNA was prepared from a 3.1 kb fragment from digestion of pA01 with HindIII and cloned in pUC119 (pCB1-H3 or pCB1-H4) and a 2.8 kb fragment from digestion of the same with SalI and cloned in pUC119 (pCB1-S1 or pCB1-S3). There were also prepared clones of the 3.1 kb HindIII fragment in pUC18 (pCB1-2, pCB1-7), a self circularized 4 kb digestion fragment from digestion of pCB1-7 with EcoRI (pCB1-b1), a clone of a 1.3 kb digestion fragment in pUC118 (pCB1a1), a self circularized 5.4 kb fragment from digestion of pCB1-7 with SalI (pCB1-c2), and clones of 2.2 kb and 0.9 kb fragments from digestion of pCB1-2 with HindIII and EcoRV, each ligated to the HindIII-HincII site of pUC18 (pCB1e1, pCB1-d1), for a total of 9 different plasmids (FIG. 1).

(4b) Preparation of Single-stranded DNA

Plasmids pCB1-H3, pCB1-H4, pCB1-S1 and pCB1-S3 were each used to transform *E. coli* JM109, and the transformed colonies were precultured overnight in LB medium containing 150 µg/ml of ampicillin. Each culturing solution was infected with an equivalent of $10^9$ PFU/ml of a helper phage M13K07 suspension. This was followed by the main culturing overnight in a 100-fold amount of LB medium containing 150 µg/ml of ampicillin and 70 µg/ml of kanamycin.

A 30 ml portion of the liquid culture was centrifuged (8000 rpm, 10 minutes) to remove the cells, and then 6 ml of PEG-NaCl (20% PEG6000, 2.5 M sodium chloride) was added to the culture supernatant to precipitate M13 particles. The PEG precipitate of M13 was suspended in 3 ml of 100 mM Tris-HCl (pH 7.5), 10 mM magnesium chloride solution and treated with 100 µg/ml of DNaseI (Behrlinger-Mannheim Co.) and 10 µg/ml of Ribonuclease A to decompose the contaminous nucleic acid of *E. coli*. After further PEG precipitation and suspension in a TE buffer solution, it was subjected to TE-saturated phenol extraction and phenol-chloroform extraction, and the single-stranded DNA was precipitated with ethanol.

(4c) Sequence Reaction and Analysis

First, the double-stranded plasmid was alkali-denatured with 2 M sodium hydroxide, and then annealed with the different primer combinations of pCB1-2 with the kit-included Universal and Reverse, pCB1-7 with Universal and Reverse, pCB1-a1 with Universal and Reverse, pCB1-b1 with Reverse, pCB1-2 with Reverse, pCB1-d1 with Reverse and pCB1e1 with Reverse, for extension reaction according to the kit protocol. In addition, sequence reaction was carried out using the combinations of pCB1-2 with WVCI-01, WVCI-02, WVCI-03, WVCI-04 and WVCI-06, and the DNA sequence of the cbh1 translated region was determined.

Sequence reaction was then carried out using the combinations of pCB1-H3 single-stranded DNA with Universal, WVCI-07, WVCI-08, WVCI-09 and WVCB-11; pCB1-H4 with WVCI-05, WVCI-15, WVCI-16 and WVCI-17; pCB1-S1 with Universal, WVCI-13, WVCI-14 and WVCB-12; and pCB1-S3 with WVCI-06, WVCI-10, WVCI-11 and WVCI-12, and the full length 4176 bp sequence of the HindIII-SalI fragment of the cbh1 gene was determined to be that listed as SEQ.ID. No.1.

The sequence of the cbh1-specific sequence primer was as follows.

```
                                              (SEQ.ID. No.14)
WVCI-01: 5'-TCA CTT TCC AGC AGC CCA ACG CC-3'

(SEQ.ID. No.15)
WVCI-02: 5'-CAA CTC TCC CAA CGC CAA GGT CG-3'

(SEQ.ID. No.16)
WVCI-03: 5'-CGT CGG GTA GGT AGA GTC CAG CC-3'

(SEQ.ID. No.17)
WVCI-04: 5'-TCT CGA ACT GAG TGA CGA CGG TC-3'

(SEQ.ID. No.18)
WVCI-05: 5'-CTG CCA TGT CAG AGG CGG GTG AG-3'

(SEQ.ID. No.19)
WVCI-06: 5'-ACT CCA ACA TCA AGT TCG GCC CC-3'

(SEQ.ID. No.20)
WVCI-07: 5'-AAC TCC CAC TGA GCC TTT ACG TC-3'

(SEQ.ID. No.21)
WVCI-08: 5'-CAA TTA AGT GGC TAA ACG TAC CG-3'

(SEQ.ID. No.22)
WVCI-09: 5'-GCA AAA ATA TAG TCG AAT CTG CC-3'

(SEQ.ID. No.23)
WVCI-10: 5'-GCT GGA ATG CTC GCT AGC TTG GC-3'

(SEQ.ID. No.24)
WVCI-11: 5'-ACT GTT GGA GAC CAG CTT GTC CG-3'

(SEQ.ID. No.25)
WVCI-12: 5'-CGC AGT AGG AGA ATA GAA ACC CC-3'

(SEQ.ID. No.26)
WVCI-13: 5'-CTG CTG TCA ATC CCC GCT ACT GG-3'

(SEQ.ID. No.27)
WVCI-14: 5'-CCT TCG AGA AAA GGA GAT TCG CG-3'

(SEQ.ID. No.28)
WVCI-15: 5'-CAG CTC CTT GGC AAA AGC AGT GG-3'

(SEQ.ID. No.29)
WVCI-16: 5'-AGA TCA TCA GTT GAG GTT AGA CC-3'

(SEQ.ID. No.30)
WVCI-17: 5'-TGT ATA AAA TTA GGT TCG GGT CC-3'

(SEQ.ID. No.31)
WVCB-11: 5'-CTA CTC ATC AAC TCA GAT CCT CC-3'

(SEQ.ID. No.32)
WVCB-12: 5'-GGA AGC CTC AGA AGT AGA TAC AGC-3'
```

(4d) Determination of Non-translated Regions ("Introns")

The introns were determined by preparing mRNA from *Trichoderma viride* MC300-1, synthesizing CDNA with reverse transcriptase, and comparing this with the genomic DNA sequence to identify the regions.

(4d-1) Preparation of Total RNA

*Trichoderma viride* MC300-1 was cultured in P medium for 2 days, and the cells were collected by centrifugation (3500 rpm, 10 minutes). The cells were washed in sterilized water and ground in a blender while frozen with liquid nitrogen. They were then suspended in a denaturing solution containing 4 M guanidine thiocyanate (4 M guanidine thiocyanate, 25 mM trisodium citrate, 0.5% sodium N-lauryl sarcosinate, 0.1 M mercaptoethanol). After a few minutes of inverting at room temperature, they were neutralized with 2 M sodium acetate (pH 4.5), and TE-saturated phenol was added prior to further inverting. Chloroform-isoamyl alcohol (24:1) was added, and inverting was followed by centrifugation (3500 rpm, 10 minutes) to remove the phenol-denatured cellular debris. The upper layer (aqueous layer) was recovered, and the nucleic acid was precipitated with isopropanol. The precipitate was recovered by centrifugation (3500 rpm, 10 minutes), and 70% ethanol-water was used for washing of the precipitate by recentrifugation.

The precipitate was dissolved in a TE buffer solution to a nucleic acid concentration of 1 mg/ml, and then precipitated with 2.5 M lithium chloride (5° C., 2 hours). The precipitate was collected by centrifugation (12,000 rpm, 10 minutes), washed with 70% ethanol and used as the total RNA fraction.

(4d-2) Preparation of polyA tail +RNA (=mRNA)

mRNA was prepared using an mRNA Purification Kit by Pharmacia Biotech Co.

First, 1 mg of the total RNA prepared in (4d-1) above was dissolved in 1 ml of an elution buffer and subjected to heat denaturation at 65° C. for 10 minutes, and after rapid cooling on ice, 0.2 ml of a sample buffer was added. The entire amount of the RNA solution was charged into an oligo(dT)

cellulose column, and after washing the column 3 times with a high-salt buffer and 3 times with a low-salt buffer, elution was performed with an elution buffer heated to 65° C. This column procedure was repeated twice to obtain the mRNA fraction.

(4d-3) Synthesis of CDNA

The cDNA was synthesized using a Timesaver cDNA Synthesis Kit by Pharmacia Biotech Co.

First, 5 μg of mRNA was dissolved in 20 μl of a sample buffer. After heat treatment at 65° C. for 10 minutes, a dithiothreitol solution and oligo(dT) primer were added together to a first strand synthesis mix for reaction at 37° C. for one hour. The entire amount was then added to a second strand mix and reacted at 12° C. for 30 minutes and then at 22° C. for one hour to obtain the cDNA.

(4d-4) Amplification of cbh1 cDNA cbh1 cDNA was amplified by the PCR using the total cDNA as the template.

The PCR was accomplished using a Takara Shuzo LA PCR Kit. The primers used were Mcbh1-N and Mcbh1-C, and the reaction was conducted by repeating 25 cycles of one minute at 94° C., 2 minutes at 55° C. and 2 minutes at 722° C. An approximately 1.6 kbp DNA fragment was amplified as a result.

The sequences of Mchbl-N and Mcbh1-C were as follows.

```
                                               (SEQ.ID. No.33)
Mcbh1-N: 5'-TCG ACT ACG GAC TGC GCA TC-3'

(SEQ.ID. No.34)
Mcbh1-C: 5'-CAA GCT TTT GCC ACA GTA CC-3'
```

After agarose electrophoresis of the PCR-amplified fragment, it was recovered from the agarose using a Band Prep Kit by Pharmacia Co., cloned in pT7-Blue by Nonagene Co. (pCbhu) and used as the intron-identifying template.

(4d-5) CDNA Sequence Analysis

The sequencing reaction was carried out using the Auto-read Sequencing Kit as well. First, plasmid pCbhU was alkali denatured with 2 M sodium hydroxide and used as the template for reaction with T7 polymerase. The primers used were the kit-included Universal and Reverse, and the aforementioned WVCI-03 and WVCI-04.

As a result, a total of two introns were found, one of 1899–1965 bp (Introne I) and one of 2663–2724 bp (Introne II). The non-translated initiation sequence and its termination sequence and the intron included regulating sequence in SEQ.ID. No.1 were as follows.

---

Introne I: 1899–1904, 1963–1965, 1946–1952
Introne II: 2663–2668, 2722–2724, 2705–2711

---

Example 5
Construction of Foreign Protein Expression Secretion Vector for *Trichoderma viride*

The cbh1 promoter, terminator and secretion signal were subjected to site-directed mutation to convert them to forms usable for the target protein expression or secretion.

(5a) Construction of Expression Vector pCB1-MX

The site-directed mutation was accomplished using a Sculptor In Vitro Mutagenesis System by Amersham Co. The mutation points were introduced upstream of the start codon and downstream of the termination codon.

First, the oligonucleotides CBn-Stu and CBc-Xho for mutation introduction were reacted at 37° C. for 15 minutes at a concentration of $0.90D_{260}$/ml using 100 mM Tris-HCl (pH 8.0), 10 mM magnesium chloride, 7 mM dithiothreitol and 1 mM PNK in ATP (Toyo Spinning Co.) for phosphorylation of the ends. They were further subjected to heat treatment at 70° C. for 10 minutes for enzyme inactivation.

CBn-Stu and CBc-Xho were each reacted with 2 μg of the aforementioned pCB1-H4 and pCB1-S1 single-stranded DNA at 70° C. for 3 minutes, and were then allowed to stand in approximately 500 ml of water at 55° C. until room temperature was reached (about 2 hours), for annealing of the oligonucleotides.

Klenow fragment and T4 ligase were reacted with the annealed mixture to synthesize heteroduplexes. The heteroduplexes were subjected to T5 exonuclease to digest the unreacted single strands. Nicks were created with restriction enzyme NciI, and the template strands were digested with exonuclease III. The mutated strands were rendered into double strands with DNA polymerase I and T4 ligase, and this was used to transform *E. coli* TG1.

For detection of the mutant DNA, the pCB1-H4-derived mutation was selected as that cleaved with StuI (pCB1H4-19) and the pCB-Sl-derived mutation was selected as that cleaved with XhoI (pCBlS1-17). Next, pCB1H4-19 was digested with XbaI and XhoI, an approximately 6 kb fragment was recovered, and this was ligated with an approximately 1.2 kb fragment obtained by digestion of pCB1S1-17 with XbaI followed by partial digestion with XhoI, resulting in pCB1-M. This was digested with XbaI, and a hygromycin B resistance cassette derived from PDH25 (Cullen, D., Leong, S. A., Wilson, L. J. and Henner, D. J., Gene 57, 21–26, 1987) was inserted to construct pCB1-MX (FIG. 2).

The sequences of CBn-Stu and CBc-Xho were as follows.

```
CBn-Stu: 5'-GAT ACA TGA TGC GCA GGC CTT AGT CGA CTA GAA TGC-3' (SEQ.ID. No.35)

CBc-Xho: 5'-GAT CCT CAA GCT TTT GCT CGA GTA CCT TAC AAG CAC-3' (SEQ.ID. No.36)
```

(5b) Construction of secretion vector pCB1-M2XR

The above pCB1-M was digested with SalI, and the approximately 2.7 kb fragment was cloned in pUC119 (pCB1-Sa1M). This was converted to single-stranded form and subjected to the same mutation as in Example 5 (5a) above using a Sculptor In Vitro Mutagenesis System. The mutation points were introduced upstream and downstream of the process residues (CB1-SmSph), into the linker domain of the cbh1 protein (CB1-Bam) and at the upstream end of the termination codon (CB1-Pst).

Figure 3:
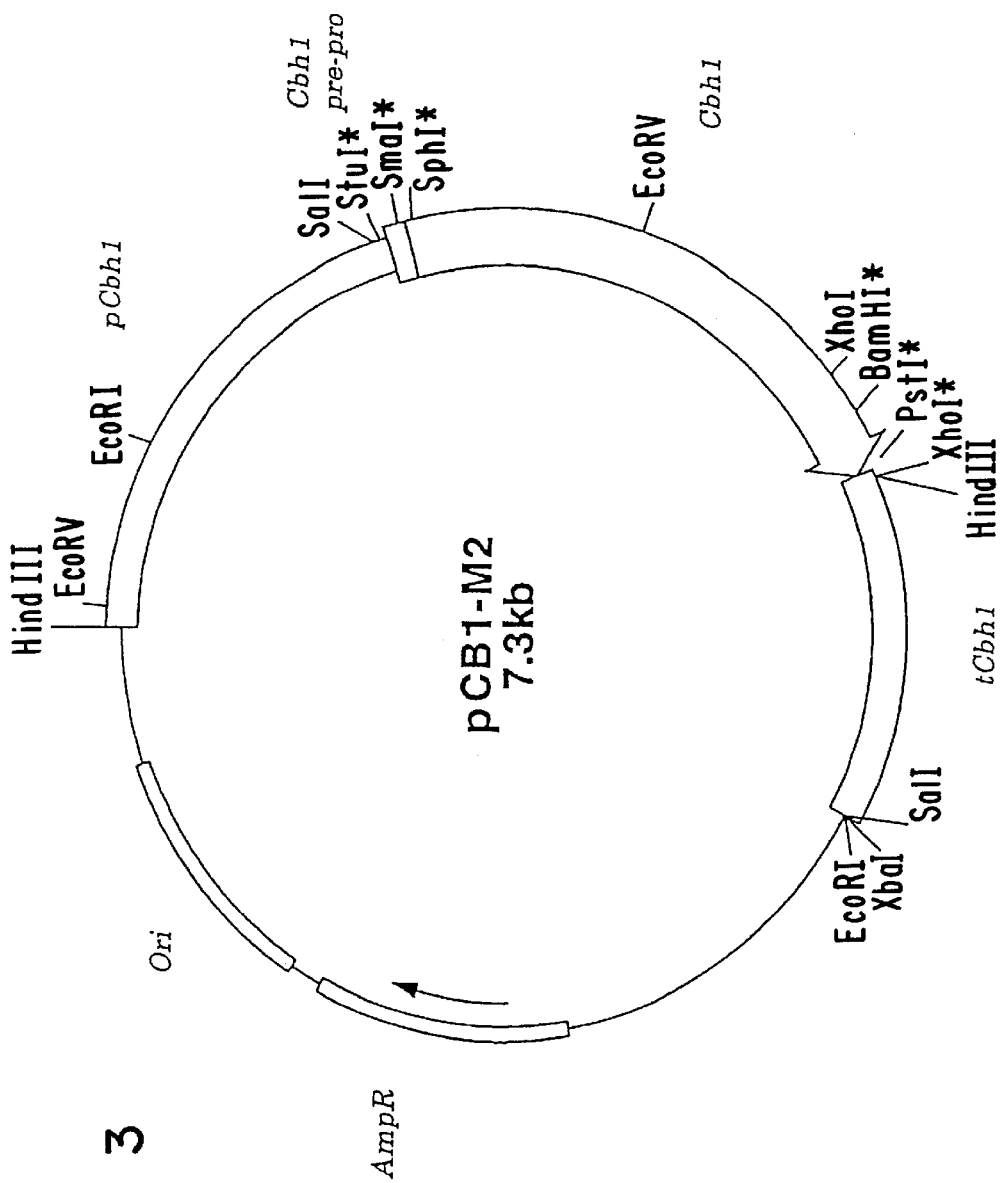
FIG. 3 is a restriction map for plasmid pCB1-M2.

The mutant gene was meanwhile constructed by cleaving pUC118 with XbaI and EcoRI and blunting the ends with a DNA Blunting Kit by Takara Shuzo. This was self circularized (pUC118-SBN) and digested with SalI and HindIII, and then ligated with the cbh1 promoter HindIII-SalI fragment. The mutation-introduced cbh1 translated region to terminator were ligated in the correct orientation at the SalI site to construct pCB1-M2 (FIG. 3). pCB1-M2XR was prepared by ligating the aforementioned hygromycin B resistance cassette to the XbaI site of pCB1-M2 (FIG. 4).

The sequences of CB1-SmSph, CB1-Bam and CB1-Pst were as follows.

```
CB1-SmSph:  5'-GGA GGG TGC ATG CCG ACT GAG CCC GGG CAG TAG     (SEQ.ID. No.37)
            CC-3'

CB1-Bam:    5'-GCC GGG AGA GGA TCC AGT GGA GG-3'                (SEQ.ID. No.38)

CB1-Pst:    5'-GCT CGA GTA CCT TAC TGC AGG CAC TGA GAG-3'       (SEQ.ID. No.39)
```

Example 6

Construction of NCE4 Secretion Vector For *Trichoderma viride*

For secretion of NCE4 in *Trichoderma viride*, the *Humicola insolens*-derived NCE4 translated region was amplified by PCR.

First, the total DNA of *Humicola insolens* was collected according to the method of Horiuchi et al. (Hiroyuki, Horiuchi et al., J. Bacteriol., 170:272–278, 1988). Specifically, *Humicola insolens* HN200-1 was cultured at 37° C. in (N) medium (5.0% Avicel, 2.0% yeast extract, 0.1% polypeptone, 0.03% calcium chloride, 0.03% magnesium sulfate, pH 6.8). After 2 days of culturing, the cells were recovered by centrifugation (3500 rpm, 10 minutes). The obtained cells were subjected to phenol treatment, Proteinase K and Ribonuclease A treatment and then polyethylene glycol (PEG) precipitation to obtain the genomic DNA.

The resulting total DNA was used as the template for PCR using Pfu polymerase (Stratagene Co.)in the presence of 1 $\mu$M of each primer HEg-mn(Sph) and HEg-c(Sal) and 200 $\mu$M of dNTPs. The PCR reaction cycle consisted of one minute of heat denaturation at 94 ° C. followed by 2 minutes of annealing at 55° C. and 5 minutes of extension reaction at 75° C., and 25 cycles were repeated to amplify the target DNA fragment.

The PCR-amplified fragment was supplied to a Microspin S-400 HR column by Pharmacia Biotech Co., and the residual primer, etc. were removed. Further digestion with SphI and SalI and agarose gel electrophoresis yielded an approximately 0.9 kb fragment.

pCB1-M2 was meanwhile digested with SphI and XhoI, and a 7.3 kb fragment was recovered. After ligating this with the 0.9 kb digested PCR fragment, the aforementioned hygromycin B resistance cassette was inserted at the XbaI site, and the constructed vector was designated as pCB1-HEgX (FIG. 5).

The DNA sequence of the NCE4 translated region obtained by this procedure was as listed in SEQ.ID. No.4.

The sequences of HEg-mn(Sph) and HEg-c(Sal) were as follows.

```
HEg-mn(Sph):  5'-GGG GCA TGC GCT GAT GGC AAG TCC ACC CG-3'      (SEQ.ID. No.40)

HEg-c(Sal):   5'-GGG GTC GAC TAC CTT ACA GGC ACT GAT GGT       (SEQ.ID. No.41)
              ACC-3'
```

Example 7

Transformation of *Trichoderma viride*

*Trichoderma viride* MC300-1 was cultured in S medium at 28° C., and after 24 hours, the cells were collected by centrifugation at 3000 rpm for 10 minutes. The resulting cells were washed with 0.5 M sucrose and then suspended in a protoplasting enzyme solution (5 mg/ml Novozyme 234, 5 mg/ml Cellulase Onozuka R-10, 0.5 M sucrose) which had been filtered with a 0.45 $\mu$m filter. The mycelia was protoplasted by shaking at 30° C. for 60–90 minutes. After filtering the suspension, the protoplasts were recovered by centrifugation at 2500 rpm for 10 minutes and washed with a SUTC buffer solution (0.5 M sucrose, 10 mM calcium chloride, 10 mM Tris-HCl (pH 7.5)).

The protoplasts prepared in this manner were suspended in 1 ml of SUTC buffer solution, and to 100 $\mu$l of this solution there was added a 10 $\mu$g DNA (TE) solution (10 $\mu$l ) prior to stationing on ice for 5 minutes. Next, 400 $\mu$l of a PEG solution (60% PEG4000, 10 mM calcium chloride, 10 mM Tris-HCl (pH 7.5)) was added, and after stationing on ice for 20 minutes, 10 ml of SUTC buffer solution was added and the mixture was centrifuged at 2500 rpm for 10 minutes. After suspending the collected protoplasts in 1 ml of SUTC buffer solution, they were centrifuged at 4000 rpm for 5 minutes and finally suspended in 100 $\mu$l of SUTC buffer solution.

These treated protoplasts were layered on hygromycin B (20 $\mu$g/ml)-added potato dextrose (PD) agar medium (3.9% potato dextrose agar, 17.1% sucrose) together with PD soft agar (1.3% potato dextrose agar, 17.1% sucrose) and cultured at 28° C. for 5 days, upon which the colonies formed were used as transformants.

Example 8

Evaluation of NCE4 Productivity by pCB1-HEgX Transformants

As in Example 7, plasmid pCB1-HEgX was introduced into *Trichoderma viride* MC300-1 and the number of strains appearing which exhibited hygromycin B resistance were about 25 strains per microgram of DNA.

After preculturing these 25 strains in S medium, the main culturing was carried out in the aforementioned P medium. The culture supernatant was analyzed by SDS- PAGE and strains appeared in which there was observed the band of approximately 43 kD molecular weight predicted for NCE4 protein.

The culture supernatant of the strain predicted to have the highest NCE4 productivity among these was fractionated with an FPLC system (product of Pharmacia Biotech Co.), and the NCE4 production was measured. The column used was a 3 ml RESOURCE RPC, and elution was performed with a 5–60% acetonitrile concentration gradient including 0.1% trifluoroacetic acid; the peak eluting at about 47% acetonitrile concentration was separated off, and upon desalting, lyophilization and measurement of the yield, 15 g of NCE4 was found per liter of liquid culture.

Example 9

Isolation and Purification of SCE3

*Trichoderma viride* MC300-1 was cultured in P medium, and the culture supernatant was subjected to hydrophobic chromatography (Phenyl-Sepharose HP 16/100, Pharmacia Biotech Co.) and eluted and fractionated with ammonium sulfate solution at a 1–0 M concentration gradient in a 50 mM acetic acid buffer solution (pH 5.5). Strong jeans decoloration activity was found in the fraction obtained with the 0.1–0 M concentration gradient, and therefore this fraction was subjected to hydrophobic chromatography (Resource PHE 30 mm. I.D.×150 mm, product of Pharmacia Biotech Co.) and eluted with ammonium sulfate solution at a 1–0 M concentration gradient in a 50 mM acetic acid buffer solution (pH 5.5), after which the active fraction was separated off.

Strong jeans decoloration activity was found in the fraction obtained with the 0 M concentration gradient. This fraction was subjected to hydrophobic chromatography (Butyl-Toyopearl 6500S 22 mm I.D.×200 mm, product of Toso Co.) and eluted with a 50 mM acetic acid buffer solution (pH 5.0), and the fraction with strong jeans decoloration activity was isolated as the purified enzyme SCE3. SCE3 showed a single band of approximately 50 kD in SDS-PAGE.

Example 10

Cloning of SCE3 Gene (10a) Analysis of N-terminal Amino Acid Sequence of SCE3 Protein Purified SCE3 obtained in the same manner as Example 9 was subjected to SDS-PAGE and transferred to a Millipore PVDF membrane (Immobilon-PSQ). The PVDF membrane was dyed with Coomassie brilliant blue, and the section in which the target protein transferred was cut out. After treatment with 0.5% polyvinylpyrrolidone 40 and 100 mM of acetic acid at 37° C. for 30 minutes, it was washed and the N-terminal modifying residues were removed with Pfu pyroglutamate aminopeptidase (50° C., 5 hours) manufactured by Takara Shuzo Co. This was subjected to a Model 492 Amino Acid Sequencer to analyze the amino acid sequence of the 10 N-terminal residues. The sequence was as follows.

SCE3-N: Gln-Asp-Val-Trp-Gly-Gln-Cys-Gly-Gly-Ile (SEQ.ID. No.42)

(10b) Peptide Map

A purified SCE3 fraction obtained in the same manner as Example 9 was digested with a 1/50 molar amount of V8 protease (Sigma Co.) in a 50 mM ammonium bicarbonate solution (pH 7.8), and the same method as in Example 1c was used to separate off three peptides, V8-18.5, V8-26 and V8-42. Their amino acid sequences were analyzed and found to be as follows.

V8-18.5: Thr-Pro-Thr-Gly-Ser-Gly- (SEQ.ID. No.43)
Asn-Ser-Trp-Thr-Asp

V8-26: Ser-Thr-Tyr-Ile-Leu-Thr- (SEQ.ID. No.44)
Glu

V8-42: Phe-Ala-Gly-Val-Asn-Ile- (SEQ.ID. No.45)
Ala-Gly-Phe-Asp-Phe-Gly-
Xaa-Thr-Thr

These amino acid sequences exhibited homology with the amino acid sequence of the protein endoglucanase III (EGIII) obtained from *Trichoderma reesei* (M. Saloheimo et al., Gene (1988), 63, 11), and therefore a gene coding for the same protein was cloned by amplifying the translated region of the EGIII gene of *Trichoderma reesei* by PCR, and it was used as a probe.

(10c) Amplification of SCE3 Translated Region

The SCE3 translated region was amplified by PCR using genomic DNA of *Trichoderma viride* MC300-1 as the template.

The amplification was carried out using Takara Taq with the *Trichoderma viride* MC300-1-derived chromosomal DNA of Example 1d as the template. SCE3-N and SCE3-C were used as the primers, and the reaction was conducted by repeating 20 cycles of one minute at 94° C., 2 minutes at 50° C. and 3 minutes at 72° C. An approximately 1.5 kbp DNA fragment was amplified as a result.

The sequences of SCE3-N and SCE3-C were as follows.

(SEQ.ID. No.46)
SCE3-N: 5'-ATG AAC AAG TCC GTG GCT C-3'

(SEQ.ID. No.47)
SCE3-C: 5'-TTA CTT TCT TGC GAG ACA CGA GC-3'

After agarose gel electrophoresis of the PCR-amplified fragment, it was recovered from the gel and used as the probe for cloning of SCE3.

(10d) Cloning of SCE3 Gene of *Trichoderma viride*

A $1.0 \times 10^4$ phage library prepared by the same method as in Example 2 was used to clone the SCE3 gene. As a result of plaque hybridization, one positive clone was obtained. Upon subjecting the clone to Southern analysis, the approximately 4 kb BamHI fragment, the approximately 4 kb EcoRI fragment and the approximately 3.7 kb XbaI fragment showed a hybridization pattern equivalent to chromosomal DNA. The XbaI fragment was cloned in pUC118 (pUC-Eg3X).

Example 11

Construction of SCE3 Expression Vector pCB1-Eg3X

In order to achieve high-yield expression of SCE3 under the control of cbh1 promoter, the translated region of SCE3 was ligated downstream from the cbh1 promoter.

First, PCR was conducted with pUC-Eg3X as the template and SCE3-Stu and SCE3-Xho as the primers, and an approximately 1.5 kb amplified fragment was recovered and subcloned in pT7-blue. The plasmid was digested with StuI and XhoI and the approximately 1.5 kb fragment was recovered. Also, pCB1-MX constructed in the same manner as in Example 5a was digested with StuI and XhoI, and the approximately 8.5 kb fragment was ligated with the approximately 1.5 kb StuI-XhoI fragment to obtain pCB1-Eg3X (FIG. 6).

The sequence of the SCE3 translated region obtained by this procedure was as listed in SEQ.ID. No.6.

The sequences of SCE3-Stu and SCE3-Xho were as follows.

SCE3-Stu: 5'-GGG AGG CCT GCG CAT CAT GGC TCC ATT GCT GCT TGC-3' (SEQ.ID. No.48)

SCE3-Xho: 5'-GGG CTC GAG TAC CTT ACT TCC TGG CGA GAC ACG AGC-3' (SEQ.ID. No.49)

Example 12
Evaluation of SCE3 Productivity by pCB1-Eg3X Transformants

Plasmid pCB1-Eg3X was introduced into *Trichoderma viride* MC300-1 in the same manner as in Example 7. As a result, the number of strains appearing which exhibited hygromycin B resistance were about 20 strains per microgram of DNA. After preculturing these 20 strains in S medium, the main culturing was carried out in P medium. The culture supernatant was analyzed by SDS-PAGE and strains appeared in which there was observed the band of approximately 50 kD molecular weight predicted for SCE3 protein.

The amount of SCE3 produced by the strain among these with the most notably observable 50 kD band (strain EG3D2) was calculated based on the decoloration activity on denim dyed cellulose-containing fibers. The specific conditions were as follows.

Desized 12 ounce blue jeans pants (cotton) were subjected to decoloration treatment under the following conditions.
Test apparatus: 20 kg washer (Sanyo SCW5101 fully automatic washer)
Bath ratio: 1:40
Heat: 60° C.
Time: 30 minutes
pH: 4 (20 mM acetic acid buffer)

The degree of decoloration was measured using a differential colorimeter, COLOR ANALYZER TOPSCAN MODEL TC-1800MK2 (product of Tokyo Denshoku, KK.), in terms of the L value (brightness) of the Lab indicator. With ΔL defined as the increase in the L value (whiteness increase) with respect to a control, the ΔL value was measured at 5 points (n=5) on each test group evaluated for decoloration, and the maximum and minimum values were discarded to take the average of the other 3 points. The protein concentration required for decoloration to a ΔL value of 4 was calculated.

The protein concentration was assayed against a γ-globulin standard using a Protein Assay Kit by Biorad Co.

In a culture supernatant of the parent strain *Trichoderma viride* MC300-1, the protein concentration required for decoloration of jeans was 160 mg/L, while the concentration was 32 mg/L for SCE3 which had been isolated and purified in Example 9. The protein concentration required for decoloration of jeans with the EG3D2 strain culture supernatant was 80 mg/L, equal to the protein concentration required for decoloration with the culture supernatant of *Trichoderma viride* MC300-1 with purified SCE3 added to 30% of the total protein content. This suggested that 30% (9 g) of the total 27 g of protein contained in one liter of the EG3D2 strain culture supernatant consisted of the (recombinant) SCE3.

Example 13
Isolation and Purification of SXY1

*Trichoderma viride* MC300-1 was cultured in P medium and the culture supernatant was purified based on xylane decomposition activity. First, it was subjected to a 6 mL Resource Q (product of Pharmacia Biotech Co.) and eluted with a 0–1 M sodium chloride concentration gradient in a 50 mM Tris-HCl (pH 7.5) buffer solution, and the fraction eluting at 0 M salt concentration was recovered. This fraction was further subjected to a 1 mL Resource HIC PHE by Pharmacia Biotech Co. and eluted with a 1.5–0 M ammonium sulfate concentration gradient in a 25 mM Tris-HCl (pH 7.0) buffer solution, and the fraction eluting at approximately 0.3 M ammonium sulfate concentration was recovered as the SXY1 fraction. This fraction was still further passed through a Superdex 75 (10/30) gel filtration column by Pharmacia Biotech Co. and developed with a 0.05 M phosphoric acid buffer solution containing 0.1 M sodium chloride, and the SXY1 fraction was recovered. SXY1 showed a single band of approximately 20 kD in SDS-PAGE.

Example 14
Cloning of SXY1 Gene (14a) Analysis of N-terminal Amino Acid Sequence of SXY1 Protein Purified SXY1 obtained in the same manner as Example 13 was subjected to SDS-PAGE and the N-terminal modifying residues were removed by the same method as in Example 10. This was subjected to a Model 492 Amino Acid Sequencer to decode the amino acid sequence of the 13 N-terminal residues. The sequence was as follows.

SXY1-N: Gln-Thr-Ile-Gly-Pro-Gly-Thr-Gly-Phe-Asn-Asn-Gly-Tyr-Phe (SEQ.ID. No.50)

This amino acid sequence exhibited homology with the amino acid sequence of the protein xylanase I (XYLI) obtained from *Trichoderma reesei* (Anneli Torronen et al., Bio/Technology (1992), 10, 1461), and therefore a gene coding for the same protein was cloned for use by amplification of the translated region of the *Trichoderma reesei* - derived XYLI gene by PCR.

(14b) Amplification of SXY1 Translated Region

The SXY1 translated region was amplified by PCR using genomic DNA of *Trichoderma viride* MC300-1 as the template.

The amplification was carried out using Takara Taq with the *Trichoderma viride* MC300-1 chromosomal DNA of Example 1d as the template. SXY1-N and SXY1-C were used as the primers, and the reaction was conducted by repeating 20 cycles of one minute at 94° C., 2 minutes at 50° C. and 3 minutes at 72° C. An approximately 0.7 kbp DNA fragment was amplified as a result.

The sequences of SXY1-N and SXY1-C were as follows.

SXY1-N: 5'-GGG AGG CCT GCG CAT CAT GGT CTC CTT CAC CTC CC-3' (SEQ.ID. No.51)

SXY1-C: 5'-GGG CTC GAG TAC CTT AGC TGA CGG TGA TGG AAG C-3' (SEQ.ID. No.52)

Example 15

Construction of SXY1 Expression Vector pCB-XI'

In order to achieve high-yield expression of SXY1 under the control of cbh1 promoter, the translated region of SXY1 was ligated downstream from the cbh1 promoter.

First, PCR was conducted in the same manner as in Example 14b, and an approximately 0.7 kb amplified fragment was recovered and subcloned in pT7-blue. The plasmid was digested with StuI and XhoI and the approximately 0.7 kb fragment was recovered. Also, pCB1-MX constructed in the same manner as in Example 5a was digested with StuI and XhoI, and the approximately 8.5 kb fragment was ligated with the approximately 0.7 kb StuI-XhoI fragment to obtain pCB-XI' (FIG. 7).

Example 16

Evaluation of SXY1 Productivity by pCB-XI' Transformants

Plasmid PCB-XI' was introduced into *Trichoderma viride* MC300-1 in the same manner as in Example 7. As a result, the number of strains appearing which exhibited hygromycin B resistance were about 10 strains per microgram of DNA. After preculturing 46 of the strains in S medium, the main culturing was carried out in P medium. The culture supernatant was analyzed by SDS-PAGE and strains appeared in which there was observed the band of approximately 20 kD molecular weight predicted for SXY1 protein.

The amount of SXY1 produced by the strain among these with the most notably observable 20 kD band (strain S22) was assayed with an FPLC system. The column used was the 1 mL Resource HIC PHE, and elution was performed with a 1–0 M ammonium sulfate concentration gradient in a 50 mM Tris-HCl (pH 7.5) buffer solution. The SXY1 production was calculated by the area ratio of the peak which eluted at approximately 0.3 M ammonium sulfate concentration, using the purified SXY1 obtained in Example 13 as a control. As a result, the SXY1 productivity of strain S22 was 8.1 g/L, which was 13 times the productivity of the parent strain.

What is claimed is:

1. A promoter sequence which comprises the nucleotide sequence of bases 1 to 1437 of SEQ ID No. 1.

2. A terminator sequence which comprises the nucleotide sequence of bases 3112 to 4167 of SEQ ID No. 1.

3. The expression vector which comprises (a) a promoter sequence comprising the nucleotide sequence of bases 1 to 1437 of SEQ ID No. 1, or (b) a terminator sequence comprising the nucleotide sequence of bases 3112 to 4167 of SEQ ID No. 1 or (c) both said promoter sequence and said terminator sequence. terminator sequences.

4. The expression vector according to claim 3, which comprises a DNA sequence coding for a target protein or peptide which is operably linked to the promoter sequence or the terminator sequence or both of the sequences.

5. The expression vector according to claim 4, wherein the target protein is an endoglucanase derived from *Humicola insolens* or a modified protein thereof.

6. The expression vector according to claim 5, wherein the endoglucanase derived from *Humicola insolens* is endoglucanase NCE4.

7. The expression vector according to claim 4, wherein the target protein is an endoglucanase derived from *Trichoderma viride* or a modified protein thereof.

8. The expression vector according to claim 7, wherein the endoglucanase derived from *Trichoderma viride* is endoglucanase SCE3.

9. The expression vector according to claim 4, wherein the target protein is a xylanase derived from *Trichoderma viride* or a modified protein thereof.

10. The expression vector according to claim 9, wherein the xylanase derived from *Trichoderma viride* is xylanase SXY1.

11. The expression vector according to claim 3, which further comprises a selection marker.

12. The expression vector according to claim 11, wherein the selection marker is a hygromycin B resistance gene.

13. Expression vector pCB1-MX, pCB1-M2XR, pCB1-HEgX, pCB1-Eg3X or pCB-XI'.

14. A host cell transformed with the expression vector according to any one of claims 3–13.

15. The host cell according to claim 14, wherein the host cell is a microorganism belonging to the genus Trichoderma.

16. The host cell according to claim 15, wherein the microorganism belonging to the genus Trichoderma kis *Trichoderma viride*.

17. The host cell according to claim 16, wherein the microorganism belonging to the genus Trichoderma is the *Trichoderma viride* high cellulase producing strain *Trichoderma viride* MC300-1, or a cell line thereof.

18. A method for producing a target protein, which comprises culturing the host cell according to claim 14 and collecting the target protein from the culture.

19. The method according to claim 18, wherein the target protein is produced at 7 g or greater per liter of liquid culture.

20. The method according to claim 18, wherein the target protein is produced at 15 g or greater per liter of liquid culture.

21. The promoter sequence according to claim 1, which has a promoter activity of expressing a target protein in an amount of about at least 7 to 8 g per liter of medium.

22. The promoter sequence according to claim 21, wherein the target protein is endoglucanase NCE4.

23. The promoter sequence according to claim 1, which has a promoter activity of expressing a target protein in an amount of about at least 15 g or more per liter of medium.

24. The promoter sequence according to claim 23, wherein the target protein is endoglucanase NCE4.

* * * * *